United States Patent
Braue, Jr. et al.

(10) Patent No.: US 7,976,832 B2
(45) Date of Patent: Jul. 12, 2011

(54) ACTIVE TOPICAL SKIN PROTECTANTS CONTAINING AMINES, POLYALKENIMINES AND /OR DERIVATIVES

(75) Inventors: Ernest H. Braue, Jr., Whiteford, MD (US); Stephen T. Hobson, Lake Forest, CA (US); Joseph D. Boecker, Baltimore, MD (US); Bryan M. Smith, Wheat Ridge, CO (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 697 days.

(21) Appl. No.: 10/429,431

(22) Filed: May 5, 2003
(Under 37 CFR 1.47)

(65) Prior Publication Data

US 2004/0067205 A1    Apr. 8, 2004

Related U.S. Application Data

(60) Provisional application No. 60/378,443, filed on May 6, 2002.

(51) Int. Cl.
 *A61K 31/74* (2006.01)
 *A61K 8/72* (2006.01)
 *A61K 8/40* (2006.01)
 *A61Q 17/04* (2006.01)
(52) U.S. Cl. .......... 424/78.02; 424/70.11; 424/59; 424/63
(58) Field of Classification Search .......... 424/78.02, 424/59, 63, 70.11
See application file for complete search history.

(56) References Cited

U.S. PATENT DOCUMENTS

| | | | |
|---|---|---|---|
| 3,714,349 A | 1/1973 | Wolverton | 424/149 |
| 4,649,037 A | 3/1987 | Marsh et al. | 423/338 |
| 5,077,316 A | 12/1991 | Bannard et al. | |
| 5,607,979 A * | 3/1997 | McCreery | 514/759 |
| 5,760,089 A | 6/1998 | Cronce | 514/643 |
| 5,904,735 A * | 5/1999 | Gutierrez et al. | 8/137 |
| 5,914,436 A | 6/1999 | Klabunde et al. | 588/205 |
| 5,990,373 A | 11/1999 | Klabunde | 588/200 |
| 6,057,488 A | 5/2000 | Koper et al. | 588/200 |
| 6,162,448 A * | 12/2000 | Nguyen et al. | 424/401 |
| 6,224,885 B1 * | 5/2001 | Jenner et al. | 424/401 |
| 6,403,653 B1 | 6/2002 | Hobson et al. | 514/759 |
| 6,410,603 B1 | 6/2002 | Hobson et al. | 514/759 |
| 6,410,604 B1 | 6/2002 | Braue et al. | 514/759 |
| 6,414,039 B1 | 7/2002 | Braue et al. | 514/759 |

(Continued)

FOREIGN PATENT DOCUMENTS

WO    WO 97/44007    11/1997

OTHER PUBLICATIONS

Audi et al. "Ricin Poisoning: A Comprehensive Review," in JAMA, Nov. 9, 2005, vol. 294, No. 18.*

(Continued)

*Primary Examiner* — Blessing M Fubara
(74) *Attorney, Agent, or Firm* — Elizabeth Arwine

(57) ABSTRACT

A topical skin protectant formulation containing a barrier cream and an active moiety for protecting warfighters and civilians against all types of harmful chemicals, specifically chemical warfare agents (CWA). The active moiety is an amine, polyalkenimines and/or derivatives. The topical skin protectant offers a barrier property and an active moiety that serves to neutralize chemical warfare agents into less toxic agents.

6 Claims, 13 Drawing Sheets

Decision Tree Network used to evaluate active TSPs.

U.S. PATENT DOCUMENTS

| | | | |
|---|---|---|---|
| 6,417,236 B1 | 7/2002 | Braue et al. | 514/759 |
| 6,420,434 B1 | 7/2002 | Braue et al. | 514/759 |
| 6,437,005 B1 | 8/2002 | Hobson et al. | 514/759 |
| 6,472,437 B1 | 10/2002 | Braue et al. | 514/759 |
| 6,472,438 B1 | 10/2002 | Braue et al. | 514/759 |
| 6,852,903 B1 * | 2/2005 | Brown et al. | 588/299 |
| 6,853,903 B2 * | 2/2005 | Michi et al. | 701/93 |

OTHER PUBLICATIONS

ATSDR, Department of Health and Human services, Agency of Toxic Substances and Disease Registry, Tox. frequently asked questions, Sep. 2003.*

Communication put out by the Centers for Disease Control and Prevention, updated Mar. 5, 2008.*

Smith, et al., Jrnl. of the American Acad of Dermatoloy, Vo. 32, No. 5, part 1, May 1995, p. 765-776, Sulfur mustard: Its continuing threatas a chemical warfare agent, the cutaneous lesions induced, progress in understanding its mechanism of action, Its long-term health effects, and new developments for protection and therapy.

Arroyo, et a, Jrnl. of Pharm. and Toxicol. Methods, vol. 33, No. 2, Apr. 1995, pp. 109-112, EPR/Spin-Label Technique as an Analytical Tool for Determining the Resistance of Reactive Topical Skin Protectants (rTSPs) to the Break through of Vesicant Agents.

* cited by examiner

```
                    ┌─────────────────┐
┌──────────────────┐│  Formulate aTSP │┌──────────────────┐
│ Sulfur Mustard,HD│└─────────────────┘│  Nerve Agent, GD │
│                  │                   │        O         │
│    Cl─S─Cl       │                   │        ‖         │
│                  │                   │     ─P─O─        │
└──────────────────┘                   │        F         │
                                       └──────────────────┘
```

Decision Tree Network used to evaluate active TSPs.

Fig. 1

DFP challenge of 2.5 wt% Lupasol WF solution as viewed with $^{31}$P NMR over 12 hours.

$^1$H NMR Spectrum of CEES in d$_6$-DMSO $^1$H NMR Spectrum of CEES + 100 eq D$_2$O in d$_6$-DMSO after 18 h.

$^1$H NMR Spectrum of CEES + 2.5 wt % Lupasol WF (ICD 3732) in 100 eq D$_2$O in d$_6$-DMSO after 12 h.

Fig. 6

Cumulative amount of HD vapor through active TSP over 20 hr.

Fig. 7

Time to GD and HD liquid breakthrough for active TSPs containing polyalkenimines.

Cumulative amount of HD and GD liquid through active TSPs over 20 hr.

Plot comparing polyalkenimines at 2.5 wt% in $D_2O$ solution against DFP challenge.

Lesion Area Ratio results of active TSPs containing polyalkenimines.

GD vapor Rabbit Lethality Test giving results of active TSPs containing polyalkenimines.

Fig. 13

VX liquid Rabbit Lethality Test giving results of active TSPs containing polyalkenimines.

Fig. 14

ACTIVE TOPICAL SKIN PROTECTANTS CONTAINING AMINES, POLYALKENIMINES AND /OR DERIVATIVES

This application claims priority of provisional application No. 60/378,443 filed May 6, 2003.

The invention described herein may be manufactured, used and licensed by or for the U.S. Government.

BACKGROUND OF THE INVENTION

1. Field of the Invention

This invention relates to active topical skin protectants. More specifically, the invention relates to an active barrier cream for protection against all types of harmful chemicals, specifically chemical warfare agents (CWAs). The active barrier cream is applied prior to exposure on the skin of persons at risk of exposure to harmful chemicals to provide a protective barrier for the skin. The active barrier cream chemically or physically reacts with harmful chemicals such as CWAs (vesicants and nerve agents) to neutralize these harmful chemicals while the barrier properties of the cream prevent penetration of harmful chemicals through the cream to the skin.

2. Description of Related Art

The concept of applying a topical protectant to vulnerable skin surfaces before entry into a chemical combat arena has been proposed as a protective measure against percutaneous CWA toxicity since the first use of CWA in World War I. The protectant was applied to vulnerable skin surfaces prior to entry into a chemical combat area. Topical protectants should augment the protection afforded by the protective over garments and/or redefine the circumstances requiring mission oriented protective posture (MOPP) levels. The rapid action of vesicating agents, also known as blistering agents, such as sulfur mustard (HD) and lewisite (L), require a pre-exposure skin protection system or a contamination avoidance approach that may preclude the percutaneous toxicity of these agents. These approaches also reduce the risk of exposure to organophosphorus (OP) chemical agents (nerve agents), which unlike the vesicating agents are lethal in droplet amounts.

An organic molecule, S-330, that reacts with CWA was incorporated into a product and fielded as the M-5 ointment kit at the end of World War II (Formula 1).

Formula 1.

S-330

However, the unacceptable barrier properties and the undesirable cosmetic properties (specifically foul odor and sticky texture) caused a recall of this product.

Two non-active topical skin protectant (TSP) formulations were developed at the United States Army Medical Research Institute of Chemical Defense (USAMRICD) and were transferred to advanced development following a Milestone Zero (MS0) Review in October 1990. The timeline of the approval of the TSP continued with MSI in 1993, a Investigational New Drug (IND) filed with the FDA in 1994, MSII in 1995, and culminated with New Drug Application (NDA) approval in February, 2000. Upon approval by the FDA, the TSP was designated Skin Exposure Reduction Paste Against Chemical Warfare Agents (SERPACWA). SERPACWA is a 50:50 (wt/wt) mixture of perfluoropolyether oil (Fomblin® Y25 from Ausimont) and poly(tetrafluoroethylene) (Polymist® F5a powder from Ausimont). The formulation described in McCreery U.S. Pat. No. 5,607,979 is directed to a topical skin protectant cream that acts as a barrier to CWA.

Although SERPACWA extends the protection afforded by MOPP and allows a longer window for decontamination, it does not completely remove the possibility for contamination because the CWA is not neutralized. To avoid contamination of other areas of the battlefield and to preclude the future percutaneous absorption of the CWA, decontamination is still required. Furthermore, although the McCreery formulation provides excellent protection against soman (GD) and sulfur mustard (HD) liquid, its protection against GD and HD vapor is minimal.

To overcome these deficiencies, there is a need for a new TSP that contains an active component. This active Topical Skin Protectant (active TSP, aTSP) was developed within the following criteria. First, the active TSP should neutralize CWA including but not limited to HD, GD, and VX. Second, the barrier properties of the TSP should be maintained or increased. Third, the protection against GD and HD vapor should increase. And fourth, the cosmetic characteristics (i. e. odor, texture) of the TSP should be maintained.

This invention meets the above criteria and solves the problems associated with the past TSPs by providing an active topical skin protectant that increases effectiveness of the TSP barrier quality and neutralizes CWA into less harmful products.

It is therefore, an objective of the present invention to provide an active topical skin protectant that prevents the percutaneous absorption of CWA and converts these toxic materials into less harmful products.

It is a further objective of the present invention to provide an active topical skin protectant that maintains desirable cosmetic properties making it acceptable to the user. Specifically, the active TSP should not be sticky, should be without offensive odor, and should be nonirritating to the skin.

It is still a further object of the invention to provide an active topical skin protectant that is practical for field operations. Specifically, the active TSP should have a stable shelf life, not be easily washed off with water, and should not react with insecticides or camouflage paint.

SUMMARY OF THE INVENTION

A topical skin protectant formulation for neutralizing chemical warfare agents into less toxic products comprising: a barrier base cream and one or more active moieties. The base cream comprises poly(tetrafluoroethylene) resins dispersed in perfluorinated polyether oils. A chemical family of active moieties that has been found to be very effective with the base cream is the polyalkenimines. Effective formulations containing polyalkenimines and other active materials in the base cream are listed in Table 1. The active barrier cream is applied to the skin prior to exposure of persons at risk of exposure to harmful chemicals to provide an active barrier to protect the skin. The active barrier cream chemically or physically reacts with harmful chemicals such as CWA to neutralize these harmful chemicals while the barrier properties of the cream prevent penetration of harmful chemicals through the cream to the skin.

BRIEF DESCRIPTION OF THE DRAWINGS

FIG. 1 is a flow diagram of the active TSP Decision Tree Network for efficacy evaluation;

FIG. 6 is a graph showing GD vapor penetration cell data of a 0.15 mm thick aTSP barrier in 20 hours;

FIG. 7 is a graph showing HD vapor penetration cell data for the cumulative amount of HD vapor through active TSP over 20 hours;

FIG. 13 is a graph showing GD vapor rabbit lethality test giving results of active TSPs containing polyalkenimines;

FIG. 14 is a graph showing VX liquid rabbit lethality test giving results of active TSPs containing polyalkenimines.

DETAILED DESCRIPTION

Candidate Active Moieties

Figure 2:
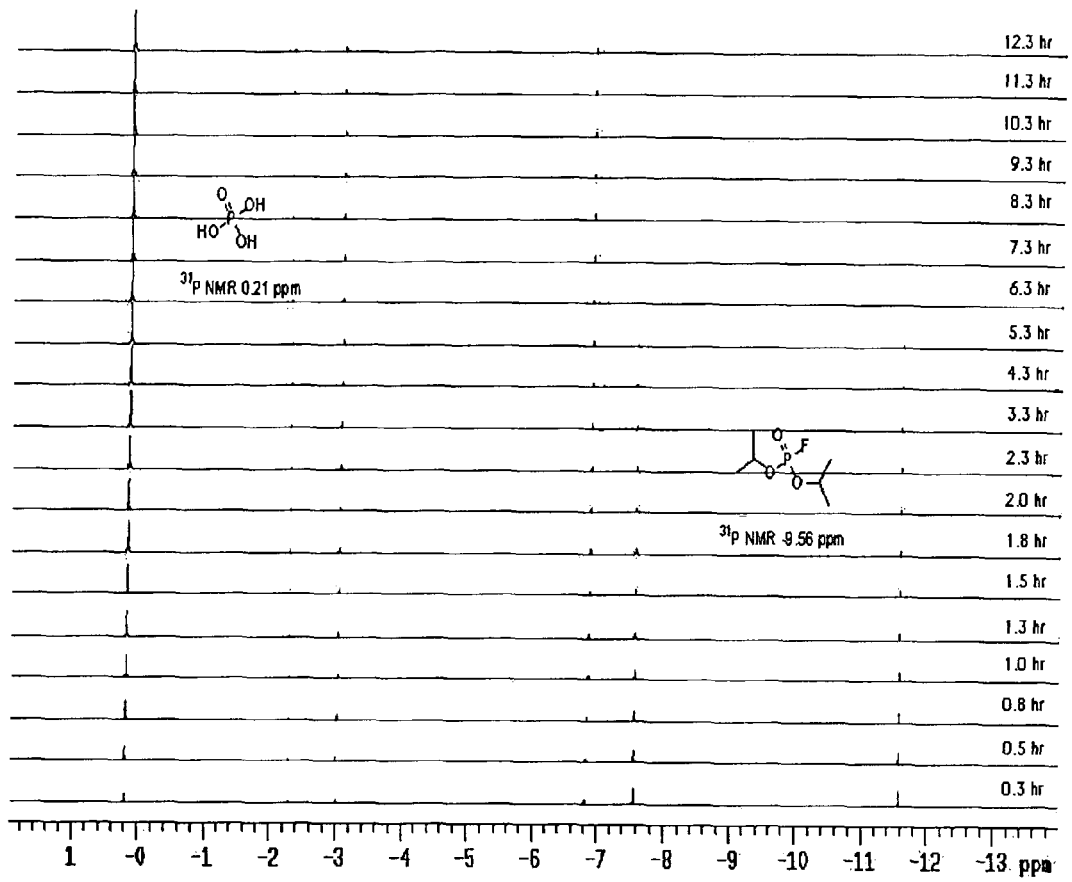
FIG. 2 is series of $^{31}$P NMR Spectra that measures the hydrolysis of Phosphorofluoridic acid diisopropyl ester (DFP) in $D_2O$ with 2.5 wt % Lupasol WF (ICD 3732)

The types of materials that neutralize harmful agents use three main modes of action: oxidation, reduction or hydrolysis.

Operating criteria, however, restricts the selection of the active materials. Thus, the active moiety must not irritate the skin, react with insecticides or camouflage paints or be lack thermal or temporal stability. This restriction eliminates many of the most active species. Furthermore, the active moiety must be incorporated into a highly fluorinated environment that is not amenable to many reaction pathways.

Table 1 is a list of formulations containing amines, polyalkenimines and/or its derivatives and other active materials that are acceptable for use in the present invention:

TABLE 1

LIST OF AMINES, POLYALKENIMINES AND/OR DERIVATIVES FOR ACTIVE TOPICAL SKIN PROTECTANTS

| ICD # | Active Moiety | % Active | % Other | % PFPE | % PTFE |
|---|---|---|---|---|---|
| 3470 | Lupasol P (ICD3720) | 10 | Fluorolink 7004 (ICD3719) 2% Water 7% | 38 | 43 |
| 3471 | Lupasol P (ICD3720) | 15 | Fluorolink 7004 (ICD3719) 3% Water 6% | 27 | 49 |
| 3630 | DEAM (ICD3604) | 2 | Light Surfactant (ICD 2853) 1% Water 1% | 49 | 46 |
| 3631 | DEAM (ICD3605) | 2 | Light Surfactant (ICD 2853) 1% Water 1% | 48 | 48 |
| 3632 | DEAM (ICD3606) | 2 | Light Surfactant (ICD 2853) 1% Water 1% | 49 | 47 |
| 3712 | Lupasol P (ICD# 3720) | 9 | Fluorolink 7004 (ICD3719, 3%), water (8%) | 48 | 32 |
| 3713 | Lupasol P (ICD# 3720) | 7 | Fluorolink 7004 (ICD3719, 3%), water (10%) | 48 | 32 |
| 3714 | Lupasol P (ICD# 3720) | 20 | Fluorolink 7004 (ICD3719, 2%), water (3%) | 60 | 15 |
| 3715 | Lupasol P (ICD# 3720) | 25 | Fluorolink 7004 (ICD3719, 2%), water (7%) | 45 | 21 |
| 3716 | Lupasol P (ICD# 3720) | 25 | Fluorolink 7004 (ICD3719, 2%), water (5%) | 43 | 25 |
| 3717 | Lupasol P (ICD# 3720) | 25 | Fluorolink 7004 (ICD3719, 2%), water (3%) | 40 | 30 |
| 3718 | Lupasol P (ICD# 3720) | 25 | Fluorolink 7004 (ICD3719, 2%), water (8%) | 35 | 30 |
| 3728 | Lupasol P (ICD# 3720) | 20 | | 55 | 25 |
| 3729 | Lupasol P (ICD# 3720) | 20 | | 40 | 40 |
| 3742 | Lupasol P (ICD# 3720) | 26 | Fluorolink 7004 (ICD#3719, 3%) | 38 | 33 |

TABLE 1-continued

LIST OF AMINES, POLYALKENIMINES AND/OR DERIVATIVES FOR ACTIVE TOPICAL SKIN PROTECTANTS

| ICD # | Active Moiety | % Active | % Other | % PFPE | % PTFE |
|---|---|---|---|---|---|
| 3743 | Lupasol P (ICD# 3720) | 26 | Fluorolink 7004 (ICD#3730, 3%) | 38 | 33 |
| 3746 | Lupasol SC (ICD# 3731) | 10 | Fluorolink 7004 (ICD3719, 2%); water (3%) | 40 | 45 |
| 3747 | Lupasol SC (ICD# 3731) | 10 | Fluorolink 7004 (ICD3719, 2%), water (8%) | 40 | 40 |
| 3748 | Lupasol SC (ICD# 3731) | 10 | Fluorolink 7005 (ICD3730, 1%), water (9%) | 40 | 40 |
| 3749 | Lupasol SC (ICD# 3731) | 15 | Fluorolink 7005 (ICD3730, 1%), water (5%) | 35 | 44 |
| 3750 | Lupasol SC (ICD# 3731) | 15 | Fluorolink 7004 (ICD3719, 2%), water (5%) | 34 | 44 |
| 3751 | Lupasol G20 (ICD# 3733) | 10 | Fluorolink 7004 (ICD3719, 2%), water (8%) | 40 | 40 |
| 3752 | Lupasol G20 (ICD# 3733) | 10 | Fluorolink 7004 (ICD3719, 2%), water (5%) | 40 | 43 |
| 3753 | Lupasol G20 (ICD# 3733) | 10 | Fluorolink 7005 (ICD3730, 1%), water (6%) | 40 | 43 |
| 3754 | Lupasol G20 (ICD# 3733) | 15 | Fluorolink 7005 (ICD3730, 1%), water (5%) | 36 | 43 |
| 3755 | Lupasol WF (ICD# 3732) | 10 | Fluorolink 7004 (ICD3719, 2%), water (8%) | 40 | 40 |
| 3756 | Lupasol WF (ICD# 3732) | 10 | Fluorolink 7004 (ICD3719, 2%), water (13%) | 40 | 35 |
| 3757 | Lupasol WF (ICD# 3732) | 10 | Fluorolink 7005 (ICD3730, 1%), water (14%) | 40 | 35 |
| 3758 | Lupasol WF (ICD# 3732) | 15 | Fluorolink 7005 (ICD3730, 1%), water (5%) | 44 | 35 |
| 3759 | Lupasol P (ICD# 3720) | 15 | Fluorolink 7005 (ICD3730, 1%), water (5%) | 44 | 36 |
| 3760 | Lupasol P (ICD# 3720) | 19 | Fluorolink 7005 (ICD3730, 1%) | 44 | 36 |
| 3771 | Lupasol P (ICD# 3720) | 26 | Fluorolink 7004 (ICD3719, 3%) | 38 | 33 |
| 3772 | Lupasol G20 (ICD# 3733) | 26 | Fluorolink 7005 (ICD3730, 3%) | 38 | 33 |
| 3773 | Lupasol G20 (ICD# 3733) | 26 | Fluorolink 7004 (ICD3719, 3%) | 38 | 33 |
| 3774 | Lupasol SC (ICD# 3731) | 26 | Fluorolink 7004 (ICD3719, 3%) | 38 | 33 |
| 3775 | Lupasol SC (ICD# 3731) | 26 | Fluorolink 7005 (ICD3730, 3%); | 38 | 33 |
| 3778 | Lupasol WF (ICD# 3732) | 26 | Fluorolink 7005 (ICD3730, 3%) | 38 | 33 |
| 3779 | Lupasol WF (ICD# 3732) | 26 | Fluorolink 7004 (ICD3719, 3%) | 38 | 33 |
| 3780 | Lupasol FG (ICD# 3766) | 26 | Fluorolink 7005 (ICD3730, 3%) | 38 | 33 |
| 3781 | Lupasol FG (ICD# 3766) | 26 | Fluorolink 7004 (ICD3719, 3%) | 38 | 33 |
| 3782 | Lupasol FG (ICD# 3766); Lupasol WF (ICD# 3732) | 13 and 13 | Fluorolink 7004 (ICD3719, 1.5%); Fluorolink 7005 (ICD3730, 1.5%) | 38 | 33 |
| 3786 | Lupasol WF (ICD# 3732) | 26 | Fluorolink 7005 (ICD3730, 3%) | 38 | 33 |
| 3787 | Lupasol WE (ICD# 3732) | 26 | Fluorolink 7004 (ICD3719, 3%) | 38 | 33 |
| 3790 | Lupasol G20 (ICD# 3733) | 26 | Fluorolink 7004 (ICD3719, 3%) | 38 | 33 |

TABLE 1-continued

LIST OF AMINES, POLYALKENIMINES AND/OR DERIVATIVES FOR ACTIVE TOPICAL SKIN PROTECTANTS

| ICD # | Active Moiety | % Active | % Other | % PFPE | % PTFE |
|---|---|---|---|---|---|
| 3791 | Lupasol WF (ICD# 3732) | 26 | Fluorolink 7005 (ICD3730, 3%) | 38 | 33 |
| 3792 | Lupasol FG (ICD# 3766) | 26 | Fluorolink 7005 (ICD3730, 3%) | 38 | 33 |
| 3793 | Lupasol P (ICD# 3720) | 24 | Fluorolink 7005 (ICD3730, 3%); water (9%) | 35 | 30 |
| 3808 | Dytek EP (ICD# 3863) | 5 | Fluorolink 7005 (ICD3730, 1%) | 49 | 45 |
| 3809 | Lupasol WF (ICD# 3732); Dytek EP | 21 and 5 | Fluorolink 7005 (ICD3730, 3%) | 38 | 33 |
| 3810 | Dytek EP (ICD# 3863) | 5 | Fluorolink 7004 (ICD3719, 3%) | 49 | 45 |
| 3811 | Lupasol FG (ICD# 3766); Dytek EP )ICD #3863) | 21 and 5 | Fluorolink 7005 (ICD3730, 3%) | 38 | 33 |
| 3829 | Lupasol P (ICD# 3720) | 26 | Fluorolink 7005 (ICD3730, 3%) | 38 | 33 |
| 3830 | Lupasol G20 (ICD# 3733) | 26 | Fluorolink 7005 (ICD3730, 3%) | 38 | 33 |
| 3831 | Lupasol SC (ICD# 3731) | 26 | Fluorolink 7005 (ICD3730, 3%) | 38 | 33 |
| 3832 | Lupasol WF (ICD# 3732) | 26 | Fluorolink 7005 (ICD3730, 3%) | 38 | 33 |
| 3833 | Lupasol FG (ICD# 3766) | 26 | Fluorolink 7004 (ICD3719, 3%) | 38 | 33 |
| 3834 | Lupasol FG (ICD# 3766); Lupasol WF (ICD# 3732) | 13 and 13 | Fluorolink 7004 (ICD3719, 1.5%) Fluorolink 7005 (ICD3730, 1.5%) | 38 | 33 |
| 3835 | Lupasol WF (ICD# 3732); Lupasol FG (ICD# 3766) | 13 and 13 | Fluorolink 7005 (ICD3730, 3%) | 38 | 33 |
| 3836 | Lupasol WF (ICD# 3732); Lupasol G20 (lCD# 3733) | 13 and 13 | Fluorolink 7005 (ICD3730, 3%) | 38 | 33 |
| 3837 | Lupasol WF (ICD# 3732); Lupasol SC (ICD# 3731) | 13 and 13 | Fluorolink 7005 (ICD3730, 3%) | 38 | 33 |
| 3838 | Lupasol WF (ICD# 3732); Lupasol P (ICD# 3720) | 13 and 13 | Fluorolink 7005 (ICD3730, 3%) | 38 | 33 |
| 3839 | Lupasol P (ICD# 3720); Lupasol FG (ICD# 3766) | 13 and 13 | Fluorolink 7005 (ICD3730, 3%) | 38 | 33 |
| 3840 | Lupasol P (ICD# 3720); Lupasol G20 (ICD# 3733) | 14 and 13 | Fluorolink 7005 (ICD3730, 3%) | 38 | 33 |
| 3841 | Lupasol P (ICD# 3720); Lupasol SC (ICD# 3731) | 13 and 13 | Fluorolink 7005 (ICD3730, 3%) | 38 | 33 |
| 3842 | Lupasol FG (ICD# 3766); Lupasol SC (ICD# 3731) | 13 and 13 | Fluorolink 7005 (ICD3730, 3%) | 38 | 33 |
| 3843 | Lupasol SC (ICD# 3731); Lupasol G20 (ICD# 3733) | 13 and 13 | Fluorolink 7005 (ICD3730, 3%) | 38 | 33 |
| 3844 | Lupasol G20 (ICD# 3733); Lupasol FG (ICD# 3766) | 11 and 12 | Fluorolink 7005 (ICD3730, 3%) | 34 | 40 |
| 3853 | Lupasol LU (ICD# 3852) | 17 | Fluorolink 7005 (ICD3730, 2%); water (4%) | 31 | 46 |
| 3854 | Lupasol LU (ICD# 3852) | 23 | Fluorolink 7005 (ICD3730, 3%) | 35 | 40 |
| 3855 | Lupasol LU (ICD# 3852) | 20 | Fluorolink 7004 (ICD3719, 1%); water (4%) | 38 | 35 |
| 3856 | Lupasol LU (ICD# 3852) | 25 | Fluorolink 7004 (ICD3719, 2%) | 38 | 35 |
| 3857 | Lupasol LU (ICD# 3852); Lupasol G20 (ICD# 3733) | 13 and 13 | Fluorolink 7005 (ICD3730, 3%) | 38 | 33 |
| 3858 | Lupasol LU (ICD# 3852); Lupasol WF (ICD# 3732) | 13 and 13 | Fluorolink 7005 (ICD3730, 3%) | 38 | 33 |
| 3859 | Lupasol LU (ICD# 3852); Lupasol SC (ICD# 3731) | 11 and 12 | Fluorolink 7005 (ICD3730, 3%) | 34 | 41 |
| 3860 | Lupasol LU (ICD# 3852); Lupasol P (ICD# 3720) | 12 and 12 | Fluorolink 7005 (ICD3730, 3%) | 35 | 38 |
| 3861 | Lupasol LU (ICD# 3852); Lupasol FG (ICD# 3766) | 12 and 12 | Fluorolink 7005 (ICD3730, 3%) | 36 | 37 |
| 3871 | PAA-HCL-3L (ICD#3867) | 23 | Fluorolink 7004 (ICD3719, 3%) | 34 | 41 |
| 3872 | PAA-HCL-3L (ICD#3867) | 26 | Fluorolink 7005 (ICD3730, 3%) | 38 | 33 |
| 3873 | PAA-10C (ICD#3868) | 19 | Fluorolink 7004 (ICD3719, 1%) | 28 | 52 |

TABLE 1-continued

LIST OF AMINES, POLYALKENIMINES AND/OR DERIVATIVES FOR
ACTIVE TOPICAL SKIN PROTECTANTS

| ICD # | Active Moiety | % Active | % Other | % PFPE | % PTFE |
|---|---|---|---|---|---|
| 3874 | PAA-10C (ICD#3868) | 18 | Fluorolink 7005 (ICD3730, 2%) | 25 | 55 |
| 3875 | PAA-HCL-3L (ICD#3867) and PAA-10C (ICD#3868) | 12 and 12 | Fluorolink 7005 (ICD3730, 3%) | 34 | 40 |
| 3884 | Lupasol WF (ICD# 3732); Lupasol G20 (ICD# 3733) | 13 and 13 | Fluorolink 7005 (ICD3730, 3%) | 38 | 33 |
| 3885 | Lupasol WF (ICD# 3732); Lupasol SC (ICD# 3731) | 13 and 13 | Fluorolink 7005 (ICD3730, 3%) | 38 | 33 |
| 3886 | Lupasol P (ICD# 3720); Lupasol FG (ICD# 3766) | 13 and 13 | Fluorolink 7005 (ICD3730, 3%) | 38 | 33 |
| 3887 | Lupasol P (ICD# 3720); Lupasol G20 (ICD# 3733) | 14 and 13 | Fluorolink 7005 (ICD3730, 3%) | 38 | 33 |
| 3900 | Lupasol P (ICD# 3720); Lupasol SC (ICD# 3731) | 13 and 13 | Fluorolink 7005 (ICD3730, 3%) | 38 | 33 |
| 3901 | Lupasol FG (ICD# 3766); Lupasol SC (ICD# 3731) | 13 and 13 | Fluorolink 7005 (ICD3730, 3%) | 38 | 33 |
| 3902 | Lupasol SC (ICD# 373); Lupasol G20 (ICD# 3733) | 13 and 13 | Fluorolink 7005 (ICD3730, 3%) | 38 | 33 |
| 3903 | Lupasol G20 (ICD# 3733 Lupasol FG (ICD# 3766) | 11 and 12 | Fluorolink 7005 (ICD3730, 3%) | 34 | 40 |
| 3970 | Lupasol WF (ICD# 3732) | 26 | Fluorolink 7004 (ICD3719 3%) | 38 | 33 |
| 3971 | Lupasol LU 321 (ICD# 3852) | 25 | Fluorolink 7004 (ICD3719, 2%) | 38 | 35 |
| 3972 | Lupasol LU 321 (ICD# 3852) | 23 | Fluorolink 7005 (ICD3730, 3%) | 35 | 40 |
| 3994 | Lupasol WF (ICD# 3732); Lupasol P (ICD# 3720) | 13 and 13 | Fluorolink 7005 (ICD3730, 3%) | 38 | 33 |
| 3997 | PAA-HCL-3L (ICD#3867) | 23 | Fluorolink 7004 (ICD3719, 3%) | 34 | 41 |
| 3998 | PAA-HCL-3L (ICD#3867) | 26 | Fluorolink 7005 (ICD3730, 3%) | 37 | 34 |
| 3999 | PAA-10C (ICD#3868) | 19 | Fluorolink 7005 (ICD3719, 1%) | 28 | 52 |
| 4000 | PAA-10C (ICD#3868) | 18 | Fluorolonk 7005 (ICD3730, 2%) | 25 | 55 |
| 4020 | Lupasol P (ICD# 3720); Lupasol G20 (ICD# 3733) | 14 and 13 | Fluorolink 7005 (ICD3730, 1.5%); Fluorolink 7004 (ICD3719, 1.5%) | 38 | 33 |
| 4021 | Lupasol P (ICD# 3720); Lupasol WF (ICD# 3732) | 13 and 13 | Fluorolink 7005 (ICD3730, 3%) | 38 | 33 |
| 4022 | Lupasol WF (IDC# 3732); Lupasol FG (ICD# 3766) | 13 and 13 | Fluorolink 7005 (ICD3730, 3%) | 38 | 33 |
| 4029 | Lupasol P (ICD# 3720) Lupasol FG (ICD# 3766) | 13 and 13 | Fluorolink 7005 (ICD3730, 1.5%); Fluorolink 7004 (ICD3719, 1.5%) | 38 | 33 |
| 4032 | Lupasol G20 (ICD# 3733) | 13 | Fluorolink 7005 (ICD3730, 2%) | 44 | 42 |
| 4033 | Lupasol G20 (ICD# 3733) | 6 | Fluorolink 7005 (ICD3730, 1%) | 47 | 46 |
| 4034 | Lupasol WF (ICD# 3732) | 13 | Fluorolink 7005 (ICD3730, 2%) | 44 | 42 |
| 4035 | Lupasol WF (ICD# 3732) | 6 | Fluorolink 7005 (ICD3730, 1%) | 47 | 46 |
| 4036 | Lupasol G20 (ICD# 3733) | 14 | Fluorolink 7004 (ICD3719, 2%) | 43 | 41 |
| 4037 | Lupasol G20 (ICD# 3733) | 7 | Fluorolink 7004 (ICD3719, 1%) | 47 | 45 |
| 4038 | Lupasol FG (ICD# 3766) | 13 | Fluorolink 7004 (ICD3719, 2%) | 44 | 42 |
| 4039 | Lupasol FG (ICD# 3766) | 7 | Fluorolink 7004 (ICD3719, 1%) | 47 | 46 |
| 4040 | Lupasol FG (ICD# 3766) | 13 | Fluorolink 7005 (ICD3730, 2%) | 44 | 41 |
| 4041 | Lupasol FG (ICD# 3766) | 7 | Fluorolink 7005 (ICD3730, 1%) | 47 | 46 |
| 4042 | Lupasol FG (ICD# 3766); Lupasol WF (ICD# 3732) | 7 and 7 | Fluorolink 7005 (ICD3730, 1%); Fluorolink 7004 (ICD3719, 1%) | 44 | 42 |

TABLE 1-continued

LIST OF AMINES, POLYALKENIMINES AND/OR DERIVATIVES FOR ACTIVE TOPICAL SKIN PROTECTANTS

| ICD # | Active Moiety | % Active | % Other | % PFPE | % PTFE |
|---|---|---|---|---|---|
| 4043 | Lupasol FG (ICD# 3766); Lupasol WF (ICD# 3732) | 3 and 3 | Fluorolink 7005 (ICD3730, 0.5%); Fluorolink 7004 (ICD3719, 0.5%) | 49 | 47 |
| 4044 | Lupasol P (ICD# 3720) | 13 | Fluorolink 7005 (ICD3730, 1.5%) | 45 | 41 |
| 4045 | Lupasol P (ICD# 3720) | 6 | Fluorolink 7005 (ICD3730, 1%) | 48 | 45 |
| 4046 | Lupasol WF (ICD# 3732) | 15 | Fluorolink 7004 (ICD3719, 2%) | 51 | 33 |
| 4047 | Lupasol P (ICD# 3720) | 14 | Fluorolink 7004 (ICD3719, 2%) | 48 | 36 |
| 4048 | Lupasol WF (ICD# 3732) | 7 | Fluorolink 7004 (ICD3719, 1%) | 50 | 41 |
| 4049 | Lupasol P (ICD# 3720) | 7 | Fluorolink 7004 (ICD3719, 1%) | 49 | 43 |
| 4050 | Lupasol P (ICD# 3720); Lupasol WF (ICD# 3732) | 13 and 13 | Fluorolink 7005 (ICD3730, 1.5%); Fluorolink 7004 (ICD3719, 1.5%) | 38 | 33 |
| 4051 | Lupasol G20 (ICD# 3733); Lupasol FG (ICD# 3766) | 13 and 13 | Fluorolink 7005 (ICD3719, 1.5%); Fluorolink 7004 (ICD3719, 1.5%) | 38 | 33 |
| 4052 | Lupasol G20 (ICD# 3733); Lupasol WF (ICD# 3732) | 13 and 13 | Fluorolink 7005 (ICD3730, 1.5%); Fluorolink 7004 (ICD3719, 1.5%) | 38 | 33 |

Abbreviations for Table 1:
PTFE: poly(tetrafluoroethylene) available as F5A powder from Ausimont, Morristown, NJ.
PFPE: perfluoropolyether available as FOMBLIM ™ Y25 oil from Ausimont, Morristown, NJ.
ICD 3719 (Fluorolink 7004 ®), available from Ausimont USA, Inc.; 1, Propene, 1,1,2,3,3,3-hexafluoro-, telomers with chlorotrifluoroethene, oxidized, reduced, ethyl ester, hydrolyzed, CAS # 220182-27-4.
LCD 3720 (Lupasol P ®), available from BASE Corp., a 50:50 wt % mixture of water and aziridine, homopolymer, CAS # 9002-98-6.
LCD 3730 (Fluorolink 7005 ®), available from Ausimont USA, Inc.; a perfluoropolyether derivative (PFPE-CONH—$(CH_2)_3$—$(OCH_2CH_3)_{18}$—$CH_3$) from Ausimont, CAS # not assigned.
ICD2853 Light PFPE Surfactant, Dupont, Wilmington, DE
ICD3731 (Lupasol SC 61B ®), available from BASE Corp., hydroxyethylated polyethylenimine, Product ID # NLE 555415. CAS #26658-46-8
ICD3732 (Lupasol WF ®) (water free), available from BASE Corp., polyethylenimine, ($CH_2$—$CH_2$—NH—)$_x$ Product ID # NLE 187702, CAS # 9002-98-6.
ICD3733 (Lupasol G20 ®) water free, available from BASE Corp., polyethylenimine, Product ID # NLE 555415, CAS # 25987-06-8.
ICD3852 (Lupasol LU 321 ®), available from BASE Corp., a 15:80:5 wt % mixture of formamide polymer (Product ID # NLE 073991) water, and sodium formate.
ICD3863 (Dytek EP ®), 1,3-pentanediamine, CAS # 589-37-7.
ICD3766 (Lupasol FG ®), available from BASE Corp., ethylenediamine-ethylenimine copolymer, ($C_2H_8N_2.C_2H_5N)_x$ Product # NCS 971991, CAS # 25987-06-8.
ICD3867 PAA-HCL-3L, 50.4 wt % aqueous solution of homopolymer of 2-propen-1-amine hydrochloride, CAS # 71550-12-4.
ICD3868 PAA-10C, 10.3 wt % aqueous solution of homopolymer of 2-propen-1-amine, CAS # 30551-89-4.

TABLE 1-continued

LIST OF AMINES, POLYALKENIMINES AND/OR DERIVATIVES FOR ACTIVE TOPICAL SKIN PROTECTANTS

| ICD # | Active Moiety | % Active | % Other | % PFPE | % PTFE |
|---|---|---|---|---|---|
| ICD3604 | Diethanolamine modified (DEAM). Cross-linked polystyrene/divinylbenzene copolymer modified with 1.2 mmol/g diethanolamine. | | | | |
| ICD3605 | Diethanolamine modified (DEAM). Cross-linked polystyrene/divinylbenzene copolymer modified with 1.5 mmol/g diethanolamine. | | | | |
| ICD 3606 | Diethanolamine modified (DEAM). Cross-linked polystyrene/divinylbenzene copolymer modified with 1.0 mmol/g diethanolamine. | | | | |

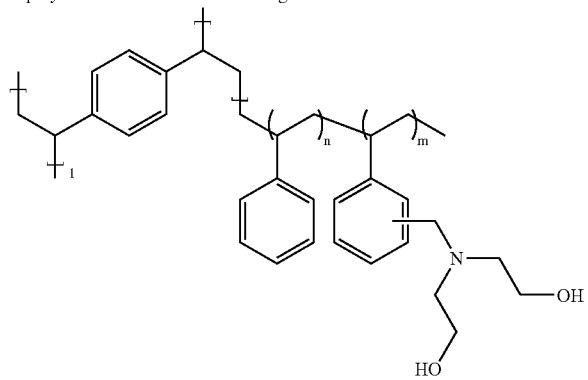

DEAM Structure (J. H. Hartley, and T. D. James, Tetrahedron Lett. 1999, 40, 2597-2600).

Examples of polyalkenimines are the polyethylenimines. These materials are available from BASF Corporation (4330 Chesapeake Dr., Charlotte, N.C.) under the trade name Lupasols.™ Lupasols (polyethylenimines, PEI) are multi-functional branched or spherical non-toxic cationic and neutral polymers. They are synthesized by the ring-opening polymerization of aziridine (ethylenimine). Depending on polymerization conditions, Lupasols contain various ratios of primary, secondary, and tertiary amines along the polymer backbone. Molecular weights also range from 800 to 2,000,000.

Polyethylenimines are synthesized from the ring opening polymerization of the nitrogen homologue of ethylene oxide. The resulting product is a highly branched, spherical polymer, which is easily protonated to form the most highly charged cationic polymer. As a result of their spherical shape and high cationic charge density, polyethylenimines are able to strongly bind onto anionic and polar surfaces. In addition, non-protonated amino groups are available to form hydrogen bonds or undergo further chemical reactions. Examples are given below:

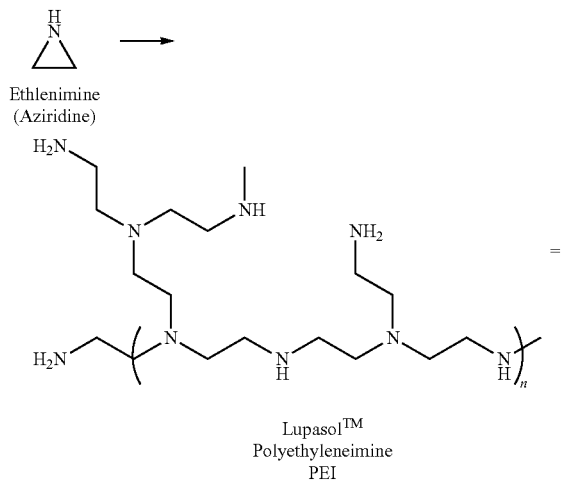

Ethlenimine (Aziridine)

Lupasol™ Polyethyleneimine PEI
Lupasol™ Synthesis

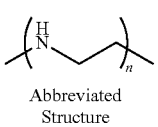

Abbreviated Structure

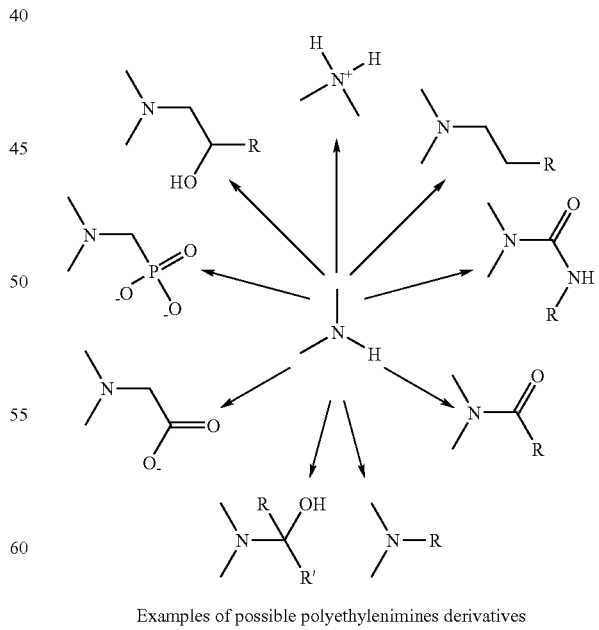

Examples of possible polyethylenimines derivatives

The percent values assigned to the above listed components of the example skin protectant formulations in Table 1 are given for example only. These values may be adjusted up or down and still embody the spirit of the invention if the herein described qualities of efficacy and composition of the present invention are met.

All active moieties listed above are useful for both liquid and vapor challenges. The amount of each varies with each formulation. The object is to optimize the quantity of active moiety in the base cream without losing the barrier properties of the base cream. The amount of active moiety can vary from about 1-30%. The amount of perfluorinated polyether oil can vary from about 30 to 60%. The amount of poly(tetrafluoroethylene) can vary from about 20 to 50%. One criterion for selection of the active materials is increased efficacy against HD and/or GD vapor. Most the listed formulations have significantly (P=0.05) increased protection compared to SERPACWA (ICD 3004) in the penetration cell model against HD and/or GD and are listed in the Results sections.

The polyalkenimines must also be incorporated into the TSP matrix without degradation of the barrier properties. These materials were incorporated into the cream either as solids or aqueous suspensions. Typically they are dispersed into the perfluorinated oil followed by sequential addition of the appropriate amount of F5A poly(tetrafluoroethylene). The TSP can contain individual polyalkenimines or mixtures of two or more polyalkenimines.

SERPACWA (ICD3004) consists of fine particles of poly(tetrafluoroethylene) resin dispersed in perfluorinated polyether oil. The excellent barrier properties of this high molecular weight polymer formulation are related to the low solubility of most materials in it. Only highly fluorinated solvents like Freon® have been observed to show appreciable solubility. This aprotic non-polar polymer mixture provides a unique medium for active moieties of the invention. Reaction mechanisms that do not involve charged transition states should be favored in this chemical environment.

Base creams formed from about 20-50% fine particulates of certain poly(tetrafluoroethylene) PTFE resins dispersed in perfluorinated polyether oils (PFPE) having viscosities from about 20 cSt to about 500 cSt afford good protection against chemical warfare agents such as HD, Lewisite (L), sulfur mustard/Lewisite mixtures (HL), pinacolyl methylphosphonofluoridate (soman or GD), thickened soman (TGD) and O-ethyl S-(2-diisopropylaminoethyl)methylphosphonothiolate (VX). PTFE and PFPE are available commercially from Ausimont (Morristown, N.J.) and Dupont (Wilmington, Del.).

The base creams used in the invention are suspensions of 20-50% finely divided PTFE having a surface area below about 6 $m^2/g$ in a perfluorinated polyether base oil prepared from poly(perfluoropropylene oxide), which has a viscosity between about 20 and about 500 cSt. More preferred compositions comprise from about 20% to about 50% of finely divided PTFE having an average particle size from about 0.1 μm to about 10 μm and a surface area below about 4 $m^2/g$ in a perfluorinated polyether base oil from 30% to 60% having a viscosity between about 20 and about 500 cSt.

Suitable perfluorinated polyether oils are Fomblin® HC- and Y-oils (Ausimont) and Krytox® oils (Dupont). The Fomblin® oils are mixtures of linear polymers based on poly(perfluoropropylene oxide) having the following chain structure: $CF_3$-[$(OCF(CF_3)CF_2)_n$-$(OCF_2CF_2)_m$]$OCF_3$. The Krytox® oils are mixtures of linear polymers also based on perfluoropropylene oxide and have the chemical structure F-[$(CF(CF_3)CF_2O)$]$_m$$CF_2CF_3$. Fomblin® Z oils having the formula: $CF_3$-[$(OCF_2CF_2)_n$-$(OCF_2)_m$]-$OCF_3$, may also be useful in the practice of the invention. The indices n and m indicate the average number of repeating polymeric subunits in the oil molecules. The oils may have a viscosity of about 20 cSt to about 500 cSt or more. The creams were generally prepared according to U.S. Pat. No. 5,607,979, incorporated herein in its entirety.

Other additives to the base cream are water and surfactant and other chemicals necessary to maintain activity. The surfactant facilitates the mixing of the water with the base cream. Examples of typical surfactants are perfluoropolyalkylether (Krytox® CAS #60164-51-4 from Dupont), Fluorolink® 7004 (1,Propene, 1,1,2,3,3,3-hexafluoro-, telomers with chlorotrifluoroethene, oxidized, reduced, ethyl ester, hydrolyzed, CAS #220182-27-4 from Ausimont), and Fluorolink® 7005 (a perfluoropolyether derivative from Ausimont, CAS # not assigned). Additional materials may also be incorporated as long as they do not reduce effectiveness of the topical protectant, such as stabilizers, camouflage paints, and sunscreens.

A further understanding of the composition of the topical protectant of the invention can be obtained by reference to certain specific example formulations set forth in Table 1. These examples are provided herein for purposes of illustration only and are not intended to be limiting. Many active moieties require the presence of water as a reagent for the hydrolysis of HD and GD. The active moieties that react by a hydrolysis mechanism require the presence of water. When the topical protectant is applied to the skin of a user, moisture in the form of perspiration may also aid in the hydrolysis of HD and GD. The addition of perfluorinated polyether surfactants to the base cream facilitates the addition of water.

Temperature and mixing sheer should be monitored to maintain the base cream at the desired consistency and quality. The active TSPs are typically prepared at ambient temperature using mechanical mixing or at controlled temperatures using either a single screw or dual screw commercial extruder (Haake® Rheomix extruder). Mixing times of 10-20 minutes are usually sufficient for dispersal of polyalkenimines into the PFPE/PTFE matrix. A typical procedure for the preparation of an active TSP with a polyalkenimine is presented below:

In a polypropylene container is added the appropriate amount of polyalkenimine (1-30% by weight) and Y25 (30-60% by weight) perfluorinated oil. The suspension is mixed with a mechanical stirrer at ambient temperature for 5 to 15 minutes or with a magnetic stirrer for 10 to 20 hours. To the suspension is added F5A poly(tetrafluoroethylene) in three portions with vigorous mechanical stirring for 5 to 10 minutes between each addition. After final addition the container is tightly capped and sealed with Parafilm®. Commercial extruders or other high-shear mixing techniques can improve the quality of the final product.

Multilayer Approach

Although an active TSP can be applied directly to the skin, the application of a powder (or liquid) that is a polyalkenimine sprinkled on the skin, or an active moiety in a base cream wherein the cream is spread on the skin, a multilayering approach can also be used. The multilayer approach would be to use the active TSP as the first layer and a solid active moiety powder (or liquid or other reactive matrix) as the second layer. The second layer would be a thin coating of the active moiety sprinkled over the active TSP cream. This approach would provide a concentrated decontamination material at the surface of the barrier cream, which would accelerate the neutralization process of CWAs coming in contact with the surface. Alternatively, the first layer can be a thin coating of the active moiety followed by a second layer of the active TSP.

Testing

Evaluation of formulations was conducted with a decision tree network (DTN) that describes the path that active TSPs follow during evaluation (FIG. 1).

The DTN is divided into two pathways: one for vesicants and the other for nerve agents. Within these pathways there are three blocks each with a decision point. The first block consists of a series of three mechanical (in vitro) modules used to determine the initial efficacy of candidate formulations and to eliminate non-effective candidates before animal testing, the second block consists of in vivo modules and the third block consists of an advanced animal module to determine the influence of time, water, sweat, and interactions with other products.

The M8 paper test is used to evaluate the barrier resistance of liquid CWA challenges, including HD, pinacolyl methylphosphonofluoridate (soman, GD), and O-ethyl S-(2-diisopropylaminoethyl) methylphosphonothioate (VX). In this test a 0.15 mm layer of active TSP is placed over a well-defined area of M8 chemical detection paper and challenged with an 8 µl droplet of CWA. When agent penetrates the active TSP barrier and reaches the M8 paper, a colored spot develops on the paper. The test assemblies are observed for 6 hr and the breakthrough time is reported for each sample. A total of nine replicates are run for each test, and a standard reference compound is included each day for quality control.

The penetration cell test is used to evaluate the barrier properties against both liquid and vapor CWA challenges (Braue, E. H. Jr. *Journal of Applied Toxicology*, 1999, 19(S), S47-S53). In this test the lower half of a Reifenrath diffusion cell (Reifenrath Consulting and Research, Richmond, Calif.) is used. A 0.15 mm thick layer of active TSP is supported by nitrocellulose paper on top of the cell. The active TSP layer is challenged with a 10-µl liquid droplet of HD or an 8 µl droplet of GD, or a saturated vapor cup of HD or GD. Breakthrough of CWA into the lower chamber of the diffusion cell is monitored using a miniature continuous air monitoring system (MINICAMS, CMS Research, Birmingham, Ala.). This system has been automated to allow continuous monitoring of five cells in a 40-min cycle. The test runs for 20 hr and the accumulated amounts of agent that break through the active TSP barrier are calculated. From these data, we obtained two values: the cumulative amount of CWA that penetrates through the active TSP, and the time at which a "breakthrough" occurs. We defined "breakthrough" values at the minimum amount of HD (1000 ng) and GD (1000 ng) that results in a physiological response. Minimal amount of HD for vesication is 1000 ng. See F. R. Sidell, J. S. Urbanetti, W. J. Smith, and C. G. Hurst in *Textbook of Military Medicine, Medical Aspects of Chemical and Biological Warfare*, edited by F. R. Sidell, E. T. Takafuji, and D. R. Franz (Office of the Surgeon General at TMM Publications, Washington, D. C. 1997) p 201. The $LD_{50}$ for soman (GD) is 350 mg/70 kg man. See F. R. Sidell in *Textbook of Military Medicine, Medical Aspects of Chemical and Biological Warfare*, edited by F. R. Sidell, E. T. Takafuji, and D. R. Franz (Office of the Surgeon General at TMM Publications, Washington, D. C. 1997) p 141. These two values allow us to rank the active TSP formulations and to select the appropriate component for advanced development.

The proof-of-neutralization test is used to verify that active TSP formulations actually neutralize CWAs into less toxic materials. This test uses the headspace solid phase microextraction (HS-SPME) technique for the collection of CWAs. Samples collected on the extraction filament are analyzed by gas chromatography/mass spectroscopy. 100 mg of active TSP formulation are challenged with 0.1 µl of neat CWA (HD, GD, or VX) in a small vial. The headspace above the mixture is sampled periodically to determine the amount of CWA remaining in the flask. Efficacy is determined by the % loss of CWA. Other analytical techniques such as Nuclear Magnetic Resonance (NMR) and Fourier-Transform Infrared Spectrometry (FTIR) have also been used in this module.

Formulations that pass this initial set of screens are moved into the second phase of testing using animal models. The weakling pig test for HD vapor evaluates a 0.15 mm thick layer of active TSP spread on the depilated dorsa. The standard saturated vapor cup is used for a 30 min challenge. The effectiveness of the active TSP is determined by measuring the degree of erythema that developed on the skin exposure site. Erythema is measured objectively using a reflectance calorimeter (see Braue, E. H. Jr. *Journal of Applied Toxicology*, 1999, 19(S), S47-S53).

The rabbit lesion area ratio (LAR) test is used to evaluate a challenge by HD liquid. In this test, a 0.15 mm layer of active TSP spread on the clipped dorsa is challenged with 1.0 µl of liquid HD spread by a 12 mm disk. The effectiveness of the active TSP is determined by measuring the lesion areas of protected and non-protected sites.

The rabbit lethality test is used to evaluate a challenge by GD vapor. In this test, a 0.15 mm layer of active TSP spread on the clipped dorsa is challenged with two vapor cups (7 $cm^2$ each) containing 28 mg GD per kg of body weight. The liquid GD is saturated onto filter paper fitted into the top of the cap so that liquid can not run down. The caps are left in place for 4 hours. After the exposure period the caps are removed and the exposure sites decontaminated. This exposure dose is lethal to all animals not protected with active TSP. The effectiveness of the active TSP is determined by lethality 1, 2, 3, 4 and 24 hr following exposure.

The guinea pig lethality test is performed by applying a 0.15 mm thick layer of active TSP on the clipped dorsa of guinea pig followed by a fixed dose of GD, TGD or VX. The effectiveness of the active TSP is determined by lethality 1, 2, 3, 4 and 24 hr following exposure.

Candidate formulations that pass the in vivo test modules move into advanced animal testing. These tests are similar to the initial animal tests with the addition of stresses for wear-time and washing with a simulated sweat solution. Interactions with other products that a warfighter might use are also evaluated. These products include camouflage paints, sunscreens and insecticides.

Results

The polyalkenimines are effective active moieties reducing the amount of HD vapor by >99% relative to the TSP alone. Although the exact mechanisms for HD neutralization are not clear, they may react by hydrolysis, direct alkylation of the polyalkenimine, or dehydrohalogenation (Scheme 1).

Scheme 1.
Possible neutralization of polyalkenimines HD.

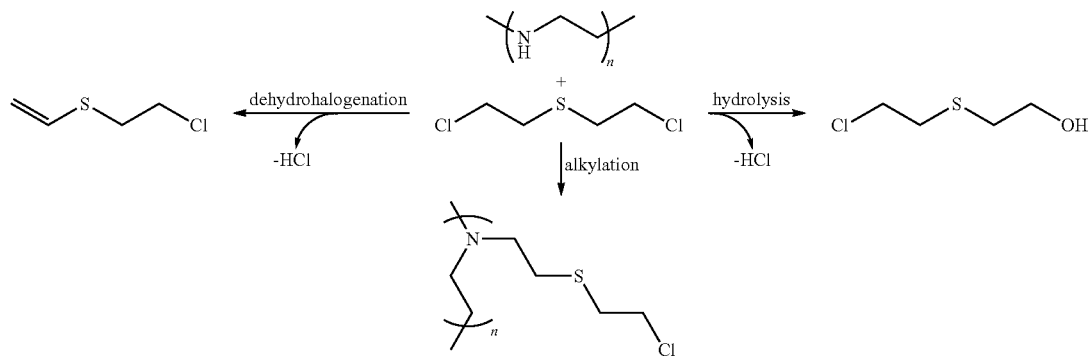

Against GD vapor the polyalkenimines reduced the amount of GD by >99% compared to TSP alone. In this case, it is likely that the polyalkenimines are active as nucleophiles or else accelerate hydrolysis through general base catalysis (Scheme 2).

The increase in protection for aTSPs formulations containing polyalkenimines was also remarkable against HD vapor as demonstrated by the decrease in total ng that break through the active TSP in 20 hours as compared to SERPACWA (ICD3004) (FIG. 7).

Scheme 2.
Hydrolyses of soman (GD) by polyalkenimines

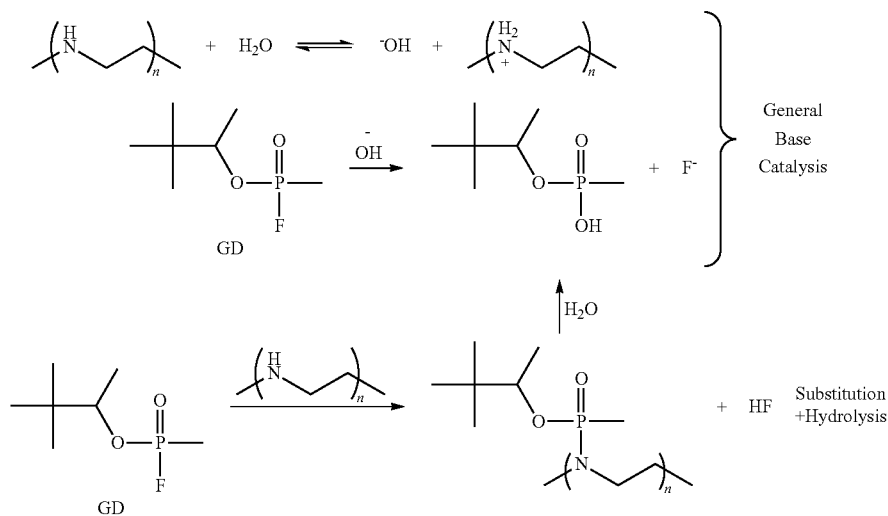

Many of the listed active TSPs contain water, and the in model reactions with a GD simulant, diisopropylfluorophosphate, (DFP), the products have FT-IR and $^{31}$p NMR spectra that are consistent with hydrolysis. Another possibility is that adventitious adsorbed water in formulations that did not have water added directly act as a reagent for this hydrolysis.

Figure 6:
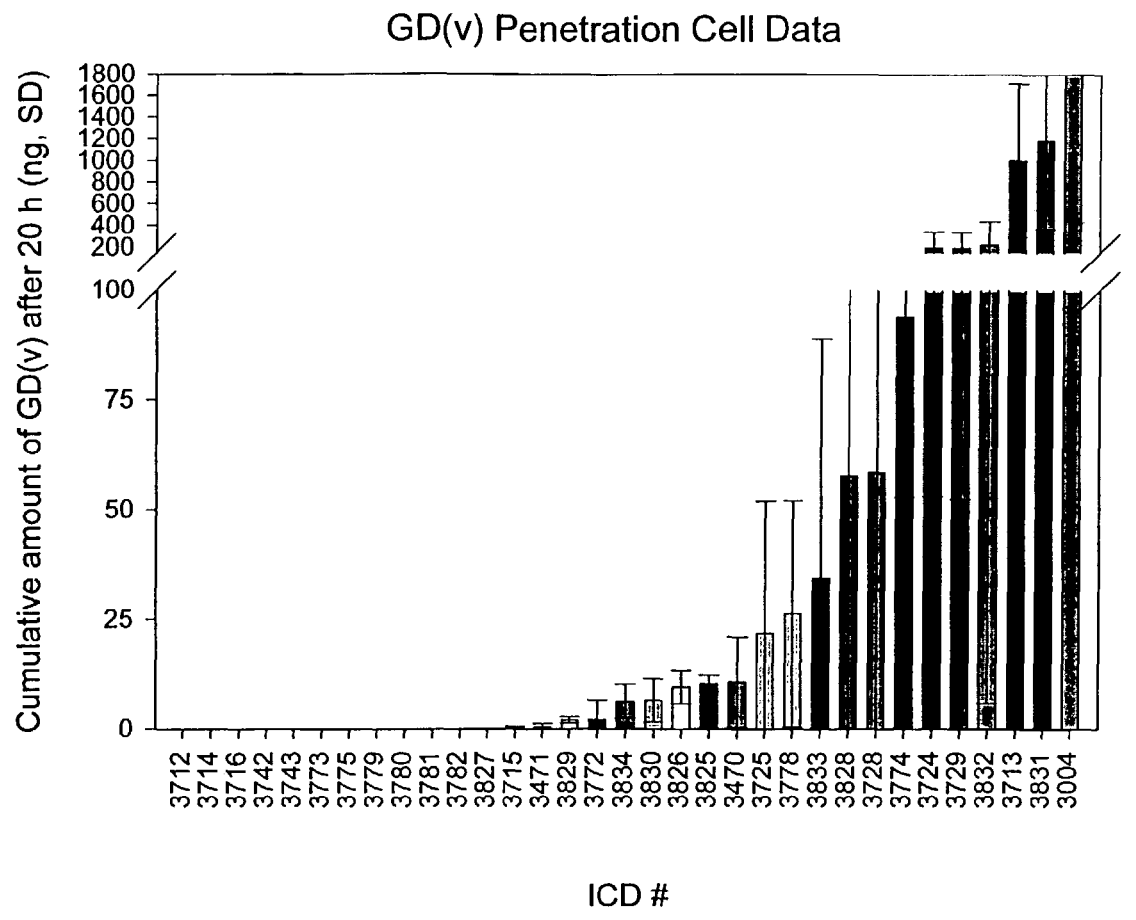

The increase in protection for the polyalkenimines was impressive against GD vapor as seen by the decrease in total ng that breakthrough the active TSP as compared to SERPACWA (ICD3004) (FIG. 6). FIG. 6 shows a total amount of GD vapor that penetrates a 0.15 mm thick aTSP barrier in 20 hr. ICD3004 (SERPACWA) is off scale with a value of 6672 ng.

Many of the formulations reduce the amount of GD vapor by >99%. Most samples display significantly (P=0.05) increased protection compared to SERPACWA (ICD 3004) in the penetration cell model against GD vapor.

As clearly seen in FIG. 7, most of the formulations containing polyalkenimines have shown outstanding protection against HD vapor in the penetration cell model. Many offer significantly better (P=0.05) protection against HD vapor compared to SERPACWA (ICD 3004).

Figure 8:
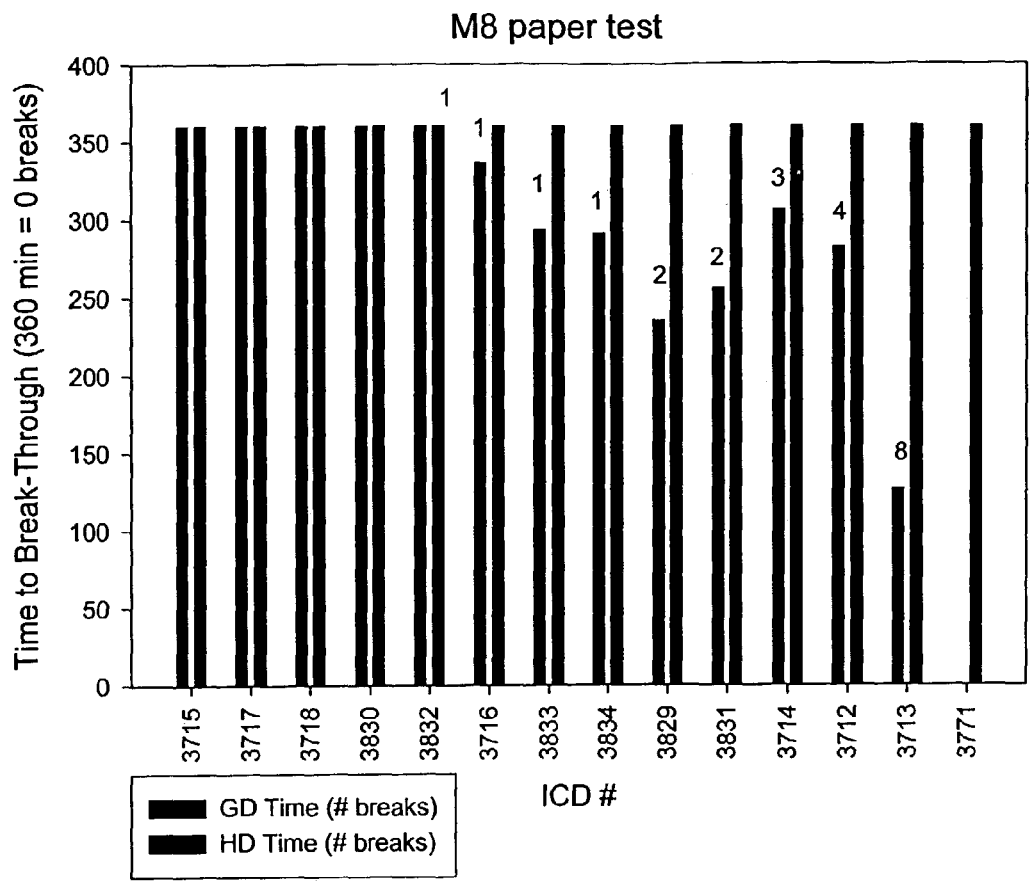
FIG. 8 is a graph showing a M8 paper test of the time to GD and HD liquid breakthrough for active TSPs containing polyalkenimines.

To roughly determine the resistance of aTSPs containing polyalkenimines, the M8 paper test was performed. All formulations tested against HD liquid proved impervious over the duration of the test (360 min) but showed variable resistance against GD liquid (FIG. 8).

Figure 9:
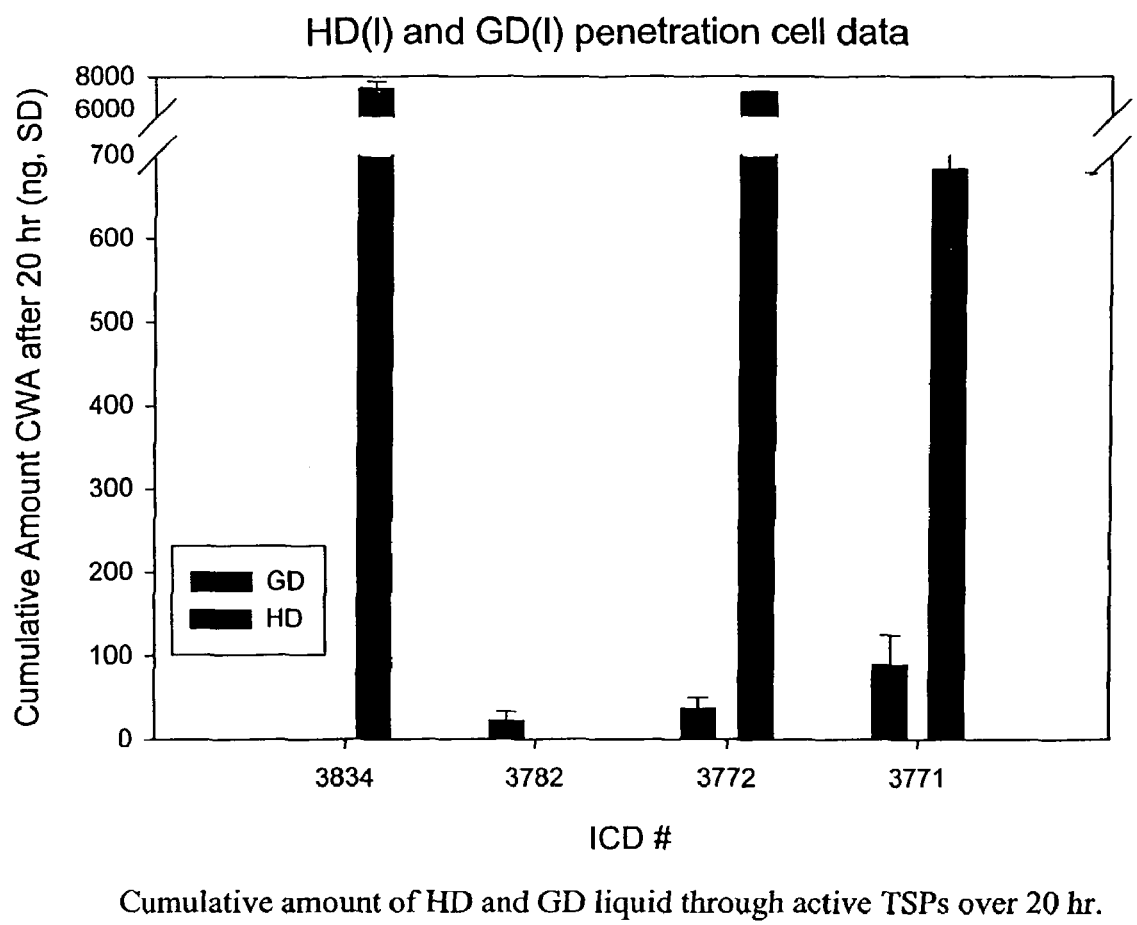
FIG. 9 is a graph showing HD liquid and GD liquid penetration cell data of the cumulative amount of HD and GD liquid through active TSP" over 20 hours.

Limited penetration cell testing has also been accomplished against HD and GD liquid. In this module, the aforementioned a TSPs performed well against GD but were ineffective against HD (FIG. 9).

Figure 10:
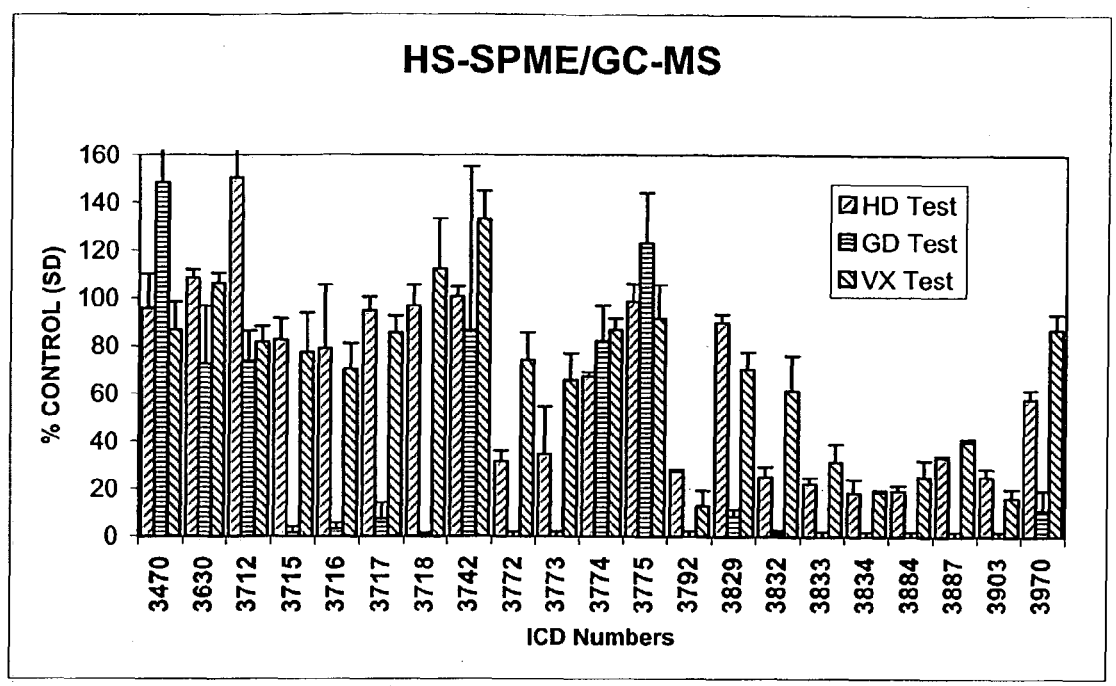
FIG. 10 is a graph showing HS-SPME/GC-MS.

In addition to the penetration cell model, certain active TSP containing polyalkenimines were tested in the headspace solid phase micro-extraction gas chromatography/mass spectrometry (HS-SPME/GC-MS) test against HD. In this module significant efficacy was seen against HD, GD, and VX (FIG. 10). For FIG. 10, evaluation of active TSPs containing polyalkenimines against HD, GD, and VX liquid using headspace solid phase micro-extraction gas chromatography/mass spectrometry (HS-SPME-GC/MS). Percent of Control is the ratio (expressed as %) of the headspace concentration of the CWA determined for each formulation divided by the headspace concentration determined for SERPACWA.

Figure 11:
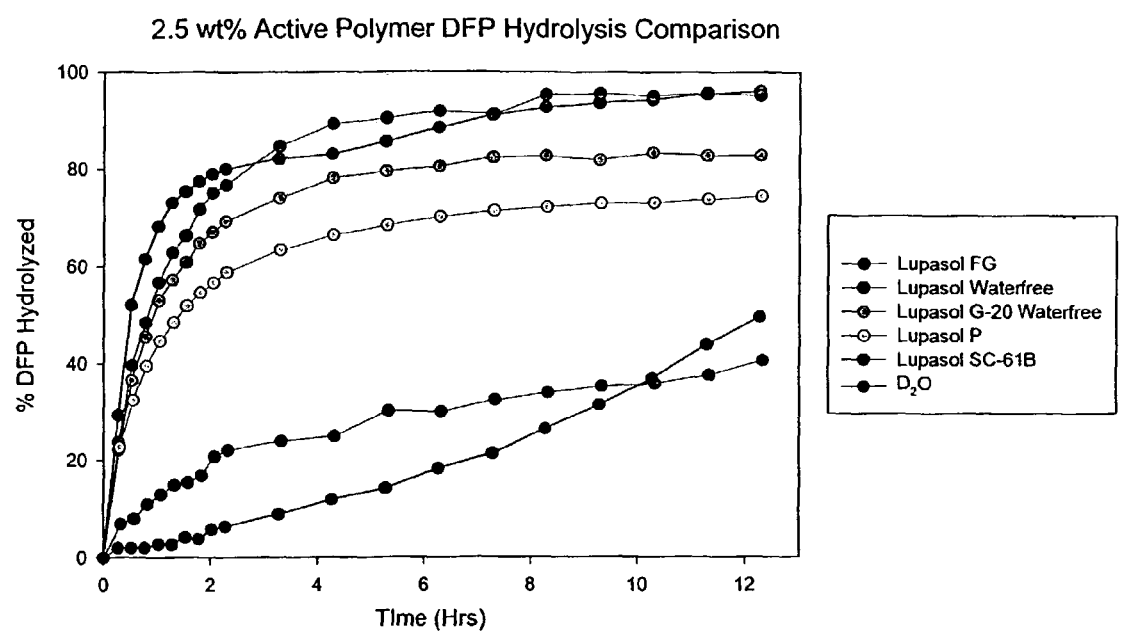
FIG. 11 is a graph comparing polyalkenimines at 2.5wt % in $D_2O$ solution against DFP challenge.

Possible neutralization pathways of these amines, polyalkenimines, and derivatives were probed using NMR with diisopropylfluorophosphate (DFP) as a GD simulant and CEES as an HD simulant. To determine the relative activity of different polyalkenimines towards organophosphates, the first experiments monitored the hydrolysis of DFP in deuterated water ($D_2O$). $^{31}P$ NMR spectra were obtained displaying both the native DFP (d, −11.6 ppm) and it hydrolysis product (s, −2.5 ppm). These spectra were obtained at regular intervals over 14 hours (FIG. 2). The extent of hydrolysis was determined by taking the ratio of the integrations of the signals for DFP and its hydrolysis product. By plotting the percent hydrolysis versus time, we were able to perform an initial ranking of the polyalkenimines (FIG. 11).

Figure 3:
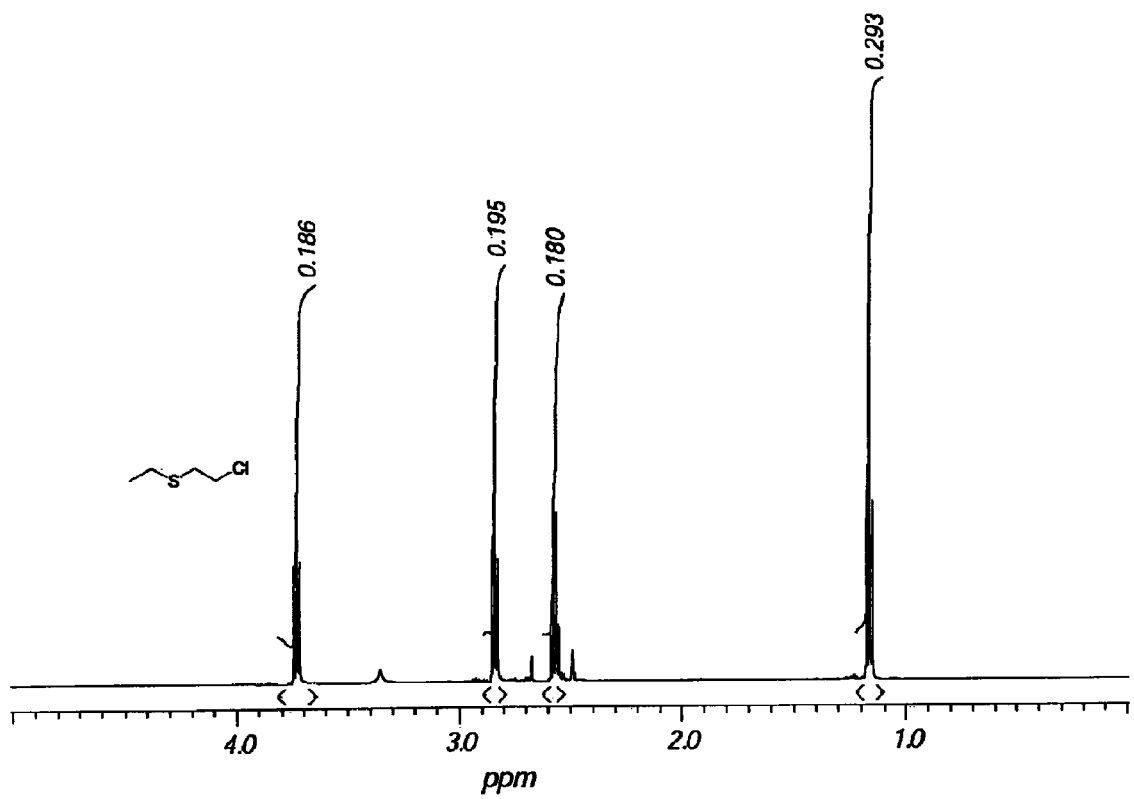
FIG. 3 is the $^1$H NMR spectrum of 2-chloroethylethylsulfide (CEES) in $d_6$-DMSO.
Figure 4:
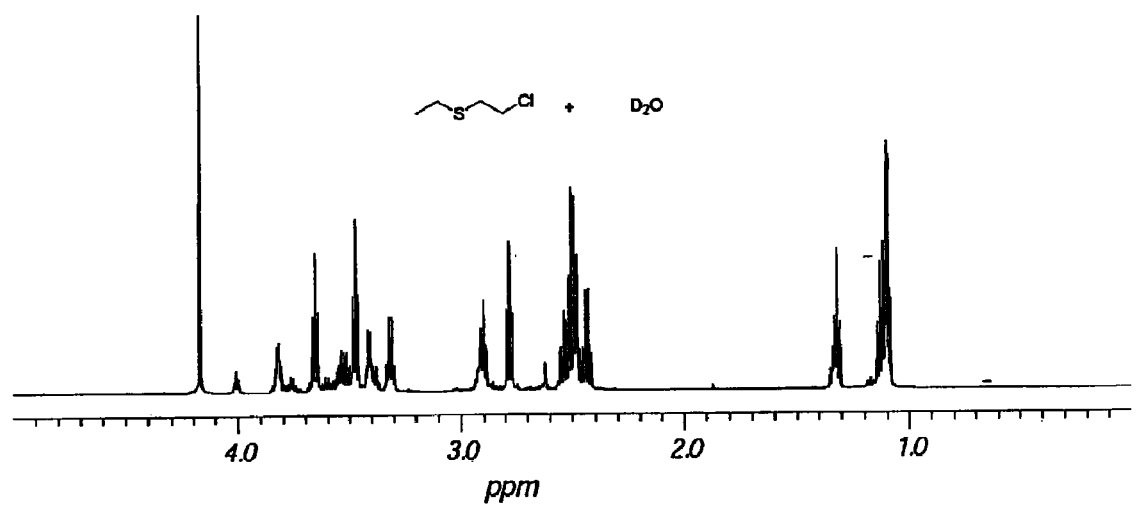
FIG. 4 is the $^1$H NMR spectrum of 2-chloroethylethylsulfide (CEES) in $d_6$-DMSO+100 eq $D_2O$ after 18 h.
Figure 5:
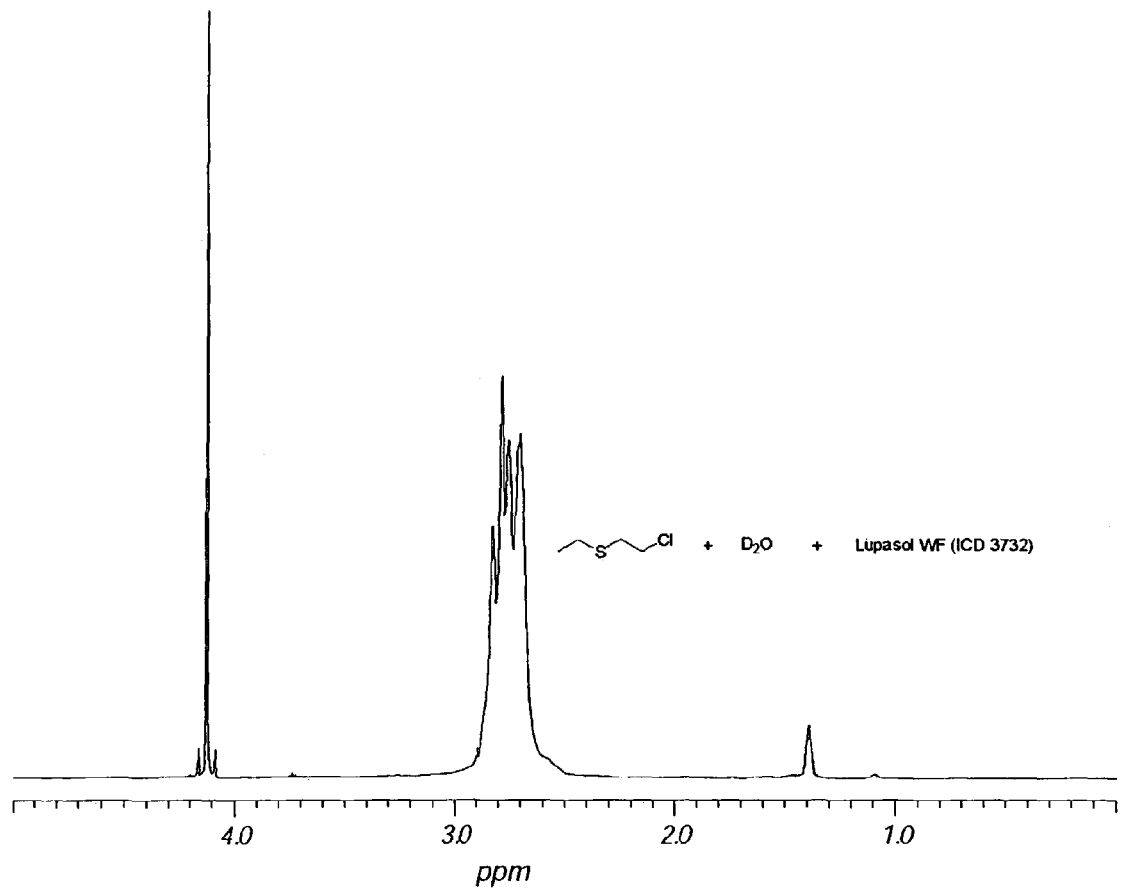
FIG. 5 is the $^1$H NMR spectrum of CEES+2.5 wt % Lupasol WF (ICD 3732) in 100 eq $D_2O$ in $d_6$-DMSO after 12 h.

To determine the possible reaction pathways for the neutralization of HD by polyalkenimines, we performed a series of experiments measuring the degree of hydrolysis in an HD simulant, 2-chloroethylethylsulfide (CEES). First, we obtained the $^1H$ NMR spectra of CEES in $d_6$-DMSO (FIG. 3). Next, we added 100 equivalents of $D_2O$ to the NMR tube and obtained $^1H$ spectra after 18 hours giving us a baseline extent of hydrolysis (FIG. 4). Finally, we prepared a standard solution of CEES in $d_6$-DMSO and added a 2.5 wt % solution of polyalkenimine in $D_2O$ (still 100 eq $D_2O$). Peak at ~4.1 ppm is from $D_2O$, broad peak from 2.5 to 3.0 ppm is from the Lupasol WF (FIG. 5). By comparing the spectra of CEES, CEES/$D_2O$ and CEES/polyalkenimine/$D_2O$, it is evident that significant hydrolysis occurs by the disappearance of CEES signals (3.75, 2.85, 2.55, 1.17 ppm).

Most of the active TSPs containing polyalkenimines also show excellent efficacy in the weanling pig HD vapor model (Table 2). The best active TSPs containing polyalkenimines almost completely eliminated erythema in this test.

TABLE 2

Weanling pig test results for HD vapor. Erythema as percentage of positive control (% of PC). Positive control has no aTSP applied. SEM is the standard error of the mean. Formulations pass the test if they offer significantly (p < 0.05) better protection than un-protected skin.

| Formulations Passing Test | | | Formulations Failing Test | | |
|---|---|---|---|---|---|
| ICD No. | % of PC | SEM | ICD No. | % of PC | SEM |
| 3470 | 56.4 | 10.5 | 3004 | 102 | 1.8 |
| 3718 | −9.6 | 17.5 | 3471 | 61.5 | 11.9 |
| 3742 | 39 | 10.6 | 3630 | 110.6 | 5.9 |
| 3743 | 41.7 | 10 | 3631 | 103.5 | 5.4 |
| 3771 | 25.1 | 7.6 | 3724 | 100.4 | 3.1 |
| 3772 | 30.8 | 7.2 | 3725 | 86.3 | 7.1 |
| 3773 | 16.3 | 3.3 | 3728 | 93.9 | 9.5 |
| 3778 | 29 | 3.2 | 3729 | 95.7 | 7.3 |
| 3779 | 43.3 | 8.5 | 3744 | 117.3 | 8.2 |
| 3780 | 28.1 | 3.8 | 3745 | 117.2 | 10.2 |
| 3781 | 39.4 | 7.3 | 3809 | 87.9 | 8.6 |
| 3782 | 16 | 3.8 | 3831 | 82.7 | 5.9 |
| 3829 | 61.7 | 9.4 | 3900 | 80.5 | 10.4 |
| 3830 | 38.9 | 7.1 | 4033 | 104.3 | 13 |
| 3832 | 26.1 | 5.7 | 4037 | 90.9 | 12.9 |
| 3833 | 15.7 | 7.3 | 4039 | 91.5 | 4 |
| 3834 | 11.6 | 5.9 | 4040 | 77.4 | 11 |
| 3884 | 23.5 | 10.7 | 4041 | 114.7 | 15.3 |
| 3885 | 70.7 | 13.1 | 4043 | 90.6 | 6.5 |
| 3886 | 46.9 | 11.8 | | | |
| 3887 | 48.3 | 9.1 | | | |
| 3901 | 73.6 | 7.4 | | | |
| 3902 | 68.5 | 5.3 | | | |
| 3903 | 50.5 | 9.5 | | | |
| 4020 | 12.4 | 11.6 | | | |
| 4021 | 35.9 | 16.7 | | | |
| 4022 | 43.4 | 13.5 | | | |
| 4029 | 25.5 | 5 | | | |
| 4032 | 54.6 | 7.7 | | | |
| 4034 | 59.7 | 7.1 | | | |
| 4036 | 46.3 | 7.6 | | | |
| 4038 | 55.5 | 6.4 | | | |
| 4042 | 59.6 | 10.9 | | | |
| 4044 | 69.6 | 7.7 | | | |
| 4046 | 13.2 | 4.6 | | | |
| 4047 | 44.3 | 6.1 | | | |
| 4048 | 66.1 | 7.2 | | | |
| 4049 | 82.8 | 6.2 | | | |
| 4050 | 13.4 | 5.4 | | | |
| 4051 | 18.6 | 7.9 | | | |
| 4052 | 10.2 | 8 | | | |

Figure 12:
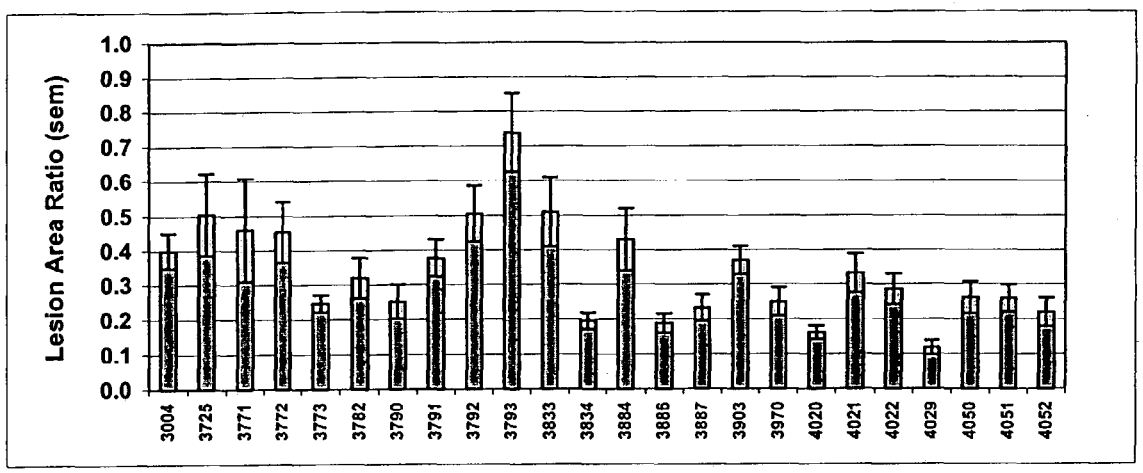
FIG. 12 is a graph showing results of active TSPs containing polyalkenimines.

All of the active TSPs containing polyalkenimines tested against HD liquid in the Lesion Area Ratio (LAR) test showed significant (p<0.05) protection compared to un-protected skin (FIG. 12). Lesion Area Ratio is the measure of the protection given by the aTSP and compares the lesion size between sites protected by aTSP with sites not protected by aTSP. Several of the formulations also demonstrate significantly improved protection compared to SERPACWA (ICD3004).

A limited number of the active TSPs containing polyalkenimines were also tested in the rabbit lethality test for GD vapor. Many show excellent efficacy. Lethality at 1, 2, 3, 4 and 24 hours post exposure from 2 vapor caps each containing 28 mg GD/kg for 4 hrs. (FIG. 13).

A limited number of the active TSPs containing polyalkenimines were also tested in the rabbit lethality test for VX liquid. Lethality at 1, 2, 3, 4 and 24 hr. post exposure to 0.5 mg VX/kg for 4 hrs. All were significantly (p <0.05) better than no protection (FIG. 14).

Having now fully described the invention, it will be apparent to one of ordinary skill in the art that many changes and modifications can be made thereto without departing from the spirit or scope of the invention as set forth herein.

What is claimed is:

1. A topical skin protectant formulation comprising:
one or more of the following formulations:

formulation 1
- a) about 10 wt % of a 50:50 mixture of water and aziridine homopolymer of average molecular weight of 750,000, and
- b) about 2 wt % of Poly(hexafluoropropylene oxide) monocarboxylic acid, chloro terminated [Cl—$(C_3F_6O)_n$—$CF_2$—COOH], and
- c) about 7 wt % water and
- d) about 48 wt % perfluoropolyether; and
- e) about 32 wt % poly(tetrafluoroethylene);

formulation 2
- a) about 7 wt % of a 50:50 mixture of water and aziridine homopolymer of average molecular weight of 750,000, and
- b) about 3 wt % of Poly(hexafluoropropylene oxide) monocarboxylic acid, chloro terminated [Cl—$(C_3F_6O)_n$—$CF_2$—COOH], and
- c) about 10 wt % water and
- d) about 48 wt % perfluoropolyether; and
- e) about 32 wt % poly(tetrafluoroethylene);

formulation 3
- a) about 20 wt % of a 50:50 mixture of water and aziridine homopolymer of average molecular weight of 750,000, and
- b) about 2 wt % of Poly(hexafluoropropylene oxide) monocarboxylic acid, chloro terminated [Cl—$(C_3F_6O)_n$—$CF_2$—COOH], and
- c) about 3 wt % water and
- d) about 60 wt % perfluoropolyether; and
- e) about 15 wt % poly(tetrafluoroethylene);

formulation 4
- a. about 25 wt % of a 50:50 mixture of water and aziridine homopolymer of average molecular weight of 750,000, and
- b. about 2 wt % of Poly(hexafluoropropylene oxide) monocarboxylic acid, chloro terminated [Cl—$(C_3F_6O)_n$—$CF_2$—COOH], and
- c. about 7 wt % water and
- d. about 45 wt % perfluoropolyether; and
- e. about 21 wt % poly(tetrafluoroethylene);

formulation 5
- a) about 25 wt % of a 50:50 mixture of water and aziridine homopolymer of average molecular weight of 750,000, and
- b) about 2 wt % of Poly(hexafluoropropylene oxide) monocarboxylic acid, chloro terminated [Cl—$(C_3F_6O)_n$—$CF_2$—COOH], and
- c) about 5 wt % water and
- d) about 43 wt % perfluoropolyether; and
- e) about 25 wt % poly(tetrafluoroethylene);

formulation 6
- a) about 25 wt % of a 50:50 mixture of water and aziridine homopolymer of average molecular weight of 750,000, and
- b) about 2 wt % of Poly(hexafluoropropylene oxide) monocarboxylic acid, chloro terminated [Cl—$(C_3F_6O)_n$—$CF_2$—COOH], and
- c) about 3 wt % water and
- d) about 40 wt % perfluoropolyether; and
- e) about 30 wt % poly(tetrafluoroethylene);

formulation 7
- a) about 25 wt % of a 50:50 mixture of water and aziridine homopolymer of average molecular weight of 750,000, and
- b) about 2 wt % of Poly(hexafluoropropylene oxide) monocarboxylic acid, chloro terminated [Cl—$(C_3F_6O)_n$—$CF_2$—COOH], and
- c) about 8 wt % water and
- d) about 35 wt % perfluoropolyether; and
- e) about 30 wt % poly(tetrafluoroethylene);

formulation 8
- a) about 10 wt % of a 50:50 mixture of water and aziridine homopolymer of average molecular weight of 750,000, and
- b) about 10 wt % water, and
- c) about 55 wt % perfluoropolyether; and
- d) about 25 wt % poly(tetrafluoroethylene);

formulation 9
- a) about 20 wt % of a 50:50 mixture of water and aziridine homopolymer of average molecular weight of 750,000, and
- b) about 40 wt % perfluoropolyether; and
- c) about 40 wt % poly(tetrafluoroethylene);

formulation 10
- a. about 26 wt % of a 50:50 mixture of water and aziridine homopolymer of average molecular weight of 750,000, and
- b. about 3 wt % of Poly(hexafluoropropylene oxide) monocarboxylic acid, chloro terminated [Cl—$(C_3F_6O)_n$—$CF_2$—COOH], and
- c. about 38 wt % perfluoropolyether; and
- d. about 33 wt % poly(tetrafluoroethylene);

formulation 11
- a) about 26 wt % of a 50:50 mixture of water and aziridine homopolymer of average molecular weight of 750,000, and
- b) about 3 wt % of Cl—$(C_3F_6O)_n$—$CF_2$—$CONH(CH_2)_m$—$(OCH_2CH_2)_n$—$(CH_2)_m$—H, and
- c) about 38 wt % perfluoropolyether; and
- d) about 33 wt % poly(tetrafluoroethylene);

formulation 12
- a) about 15 wt % of a 50:50 mixture of water and aziridine homopolymer of average molecular weight of 750,000, and
- b) about 1 wt % of Cl—$(C_3F_6O)_n$—$CF_2$—$CONH(CH_2)_m$—$(OCH_2CH_2)_n$—$(CH_2)_m$—H, and
- c) about 44 wt % perfluoropolyether; and
- d) about 36 wt % poly(tetrafluoroethylene), and
- e) about 5 wt % water;

formulation 13
- a) about 19 wt % of a 50:50 mixture of water and aziridine homopolymer of average molecular weight of 750,000, and
- b) about 1 wt % of Cl—$(C_3F_6O)_n$—$CF_2$—$CONH(CH_2)_m$—$(OCH_2CH_2)_n$—$(CH_2)_m$—H, and
- c) about 44 wt % perfluoropolyether; and
- d) about 36 wt % poly(tetrafluoroethylene);

formulation 14
- a) about 24 wt % of a 50:50 mixture of water and aziridine homopolymer of average molecular weight of 750,000, and
- b) about 3 wt % of Cl—$(C_3F_6O)_n$—$CF_2$—$CONH(CH_2)_m$—$(OCH_2CH_2)_n$—$(CH_2)_m$—H, and
- c) about 35 wt % perfluoropolyether; and
- d) about 30 wt % poly(tetrafluoroethylene), and
- e) about 9 wt % water;

formulation 15
  a) about 10 wt % of polyaziridine of average molecular weight of 25,000, and
  b) about 2 wt % of Poly(hexafluoropropylene oxide) monocarboxylic acid, chloro terminated [Cl—$(C_3F_6O)_n$—$CF_2$—COOH], and
  c) about 8 wt % water, and
  d) about 40 wt % perfluoropolyether; and
  e) about 40 wt % poly(tetrafluoroethylene);
formulation 16
  a) about 10 wt % of polyaziridine of average molecular weight of 25,000, and
  b) about 2 wt % of Poly(hexafluoropropylene oxide) monocarboxylic acid, chloro terminated [Cl—$(C_3F_6O)_n$—$CF_2$—COOH], and
  c) about 13 wt % water, and
  d) about 40 wt % perfluoropolyether; and
  e) about 35 wt % poly(tetrafluoroethylene);
formulation 17:
  a. about 10 wt % of polyaziridine of average molecular weight of 25,000, and
  b. about 1 wt % of Cl—$(C_3F_6O)_n$—$CF_2$—$CONH(CH_2)_m$—$(OCH_2CH_2)_n$—$(CH_2)_m$—H, and
  c. about 14 wt % water, and
  d. about 40 wt % perfluoropolyether; and
  e. about 35 wt % poly(tetrafluoroethylene);
formulation 18
  a) about 15 wt % of polyaziridine of average molecular weight of 25,000, and
  b) about 1 wt % of Cl—$(C_3F_6O)_n$—$CF_2$—$CONH(CH_2)_m$—$(OCH_2CH_2)_n$—$(CH_2)_m$—H, and
  c) about 5 wt % water, and
  d) about 44 wt % perfluoropolyether; and
  e) about 35 wt % poly(tetrafluoroethylene);
formulation 19
  a) about 26 wt % of polyaziridine of average molecular weight of 25,000, and
  b) about 3 wt % of Cl—$(C_3F_6O)_n$—$CF_2$—$CONH(CH_2)_m$—$(OCH_2CH_2)_n$—$(CH_2)_m$—H, and
  c) about 38 wt % perfluoropolyether; and
  d) about 33 wt % poly(tetrafluoroethylene);
formulation 20
  a) about 26 wt % of polyaziridine of average molecular weight of 25,000, and
  b) about 3 wt % of Poly(hexafluoropropylene oxide) monocarboxylic acid, chloro terminated [Cl—$(C_3F_6O)_n$—$CF_2$—COOH], and
  c) about 38 wt % perfluoropolyether; and
  d) about 33 wt % poly(tetrafluoroethylene);
formulation 21
  a) about 21 wt % of polyaziridine of average molecular weight of 25,000, and
  b) about 5 wt % 1, 3-pentanediamine, and
  c) about 3 wt % of Cl—$(C_3F_6O)_n$—$CF_2$—$CONH(CH_2)_m$—$(OCH_2CH_2)_n$—$(CH_2)_m$—H, and
  d) about 38 wt % perfluoropolyether; and
  e) about 33 wt % poly(tetrafluoroethylene);
formulation 22
  a) about 10 wt % of polyaziridine of average molecular weight of 1300, and
  b) about 2 wt % of Poly(hexafluoropropylene oxide) monocarboxylic acid, chloro terminated [Cl—$(C_3F_6O)_n$—$CF_2$—COOH], and
  c) about 8 wt % water and
  d) about 40 wt % perfluoropolyether; and
  e) about 40 wt % poly(tetrafluoroethylene);
formulation 23
  a) about 10 wt % polyaziridine of average molecular weight of 1300, and
  b) about 2 wt % of Poly(hexafluoropropylene oxide) monocarboxylic acid, chloro terminated [Cl—$(C_3F_6O)_n$—$CF_2$—COOH], and
  c) about 5 wt % water and
  d) about 40 wt % perfluoropolyether; and
  e) about 43 wt % poly(tetrafluoroethylene);
formulation 24
  a) about 10 wt % polyaziridine of average molecular weight of 1300, and
  b) about 1 wt % of Cl—$(C_3F_6O)_n$—$CF_2$—$CONH(CH_2)_m$—$(OCH_2CH_2)_n$—$(CH_2)_m$—H, and
  c) about 6 wt % water and
  d) about 40 wt % perfluoropolyether; and
  e) about 43 wt % poly(tetrafluoroethylene);
formulation 25
  a) about 15 wt % polyaziridine of average molecular weight of 1300, and
  b) about 1 wt % of Cl—$(C_3F_6O)_n$—$CF_2$—$CONH(CH_2)_m$—$(OCH_2CH_2)_n$—$(CH_2)_m$—H, and
  c) about 5 wt % water and
  d) about 36 wt % perfluoropolyether; and
  e) about 43 wt % poly(tetrafluoroethylene);
formulation 26
  a) about 26 wt % polyaziridine of average molecular weight of 1300, and
  b) about 3 wt % of Cl—$(C_3F_6O)_n$—$CF_2$—$CONH(CH_2)_m$—$(OCH_2CH_2)_n$—$(CH_2)_m$—H, and
  c) about 38 wt % perfluoropolyether; and
  d) about 33 wt % poly(tetrafluoroethylene);
formulation 27:
  a) about 26 wt % polyaziridine of average molecular weight of 1300, and
  b) about 3 wt % of Poly(hexafluoropropylene oxide) monocarboxylic acid, chloro terminated [Cl—$(C_3F_6O)_n$—$CF_2$—COOH], and
  c) about 38 wt % perfluoropolyether; and
  d) about 33 wt % poly(tetrafluoroethylene);
formulation 28
  a) about 10 wt % hydroxyethylated polyaziridine with average molecular weight of 110,000, and
  b) about 2 wt % of Poly(hexafluoropropylene oxide) monocarboxylic acid, chloro terminated [Cl—$(C_3F_6O)_n$—$CF_2$—COOH], and
  c) about 40 wt % perfluoropolyether; and
  d) about 45 wt % poly(tetrafluoroethylene), and
  e) about 3 wt % water;
formulation 29
  a) about 10 wt % hydroxyethylated polyaziridine with average molecular weight of 110,000, and
  b) about 2 wt % of Poly(hexafluoropropylene oxide) monocarboxylic acid, chloro terminated [Cl—$(C_3F_6O)_n$—$CF_2$—COOH], and
  c) about 8 wt % water and
  d) about 40 wt % perfluoropolyether; and
  e) about 40 wt % poly(tetrafluoroethylene);
formulation 30
  a) about 10 wt % hydroxyethylated polyaziridine with average molecular weight of 110,000, and
  b) about 1 wt % of Poly(hexafluoropropylene oxide) monocarboxylic acid, chloro terminated [Cl—$(C_3F_6O)_n$—$CF_2$—COOH], and
  c) about 9 wt % water and
  d) about 40 wt % perfluoropolyether; and
  e) about 40 wt % poly(tetrafluoroethylene);

formulation 31
- a) about 15 wt % hydroxyethylated polyaziridine with average molecular weight of 110,000, and
- b) about 1 wt % of Cl—$(C_3F_6O)_n$—$CF_2$—$CONH(CH_2)_m$—$(OCH_2CH_2)_n$—$(CH_2)_m$—H, and
- c) about 5 wt % water and
- d) about 35 wt % perfluoropolyether; and
- e) about 44 wt % poly(tetrafluoroethylene);

formulation 32
- a) about 15 wt % hydroxyethylated polyaziridine with average molecular weight of 110,000, and
- b) about 2 wt % of Poly(hexafluoropropylene oxide) monocarboxylic acid, chloro terminated [Cl—$(C_3F_6O)_n$—$CF_2$—COOH], and
- c) about 5 wt % water and
- d) about 34 wt % perfluoropolyether; and
- e) about 44 wt % poly(tetrafluoroethylene);

formulation 33
- a) about 26 wt % hydroxyethylated polyaziridine with average molecular weight of 110,000, and
- b) about 3 wt % of Poly(hexafluoropropylene oxide) monocarboxylic acid, chloro terminated [Cl—$(C_3F_6O)_n$—$CF_2$—COOH], and
- c) about 38 wt % perfluoropolyether; and
- d) about 33 wt % poly(tetrafluoroethylene);

formulation 34
- a. about 26 wt % hydroxyethylated polyaziridine with average molecular weight of 110,000, and
- b. about 3 wt % of Cl—$(C_3F_6O)_n$—$CF_2$—$CONH(CH_2)_m$—$(OCH_2CH_2)_n$—$(CH_2)_m$—H, and
- c. about 38 wt % perfluoropolyether; and
- d. about 33 wt % poly(tetrafluoroethylene);

formulation 35
- a) about 26 wt % of ethylenediamine-aziridine copolymer of average molecular weight of 800, and
- b) about 3 wt % of Cl—$(C_3F_6O)_n$—$CF_2$—$CONH(CH_2)_m$—$(OCH_2CH_2)_n$—$(CH_2)_m$—H, and
- c) about 38 wt % perfluoropolyether; and
- d) about 33 wt % poly(tetrafluoroethylene);

formulation 36
- a) about 26 wt % of ethylenediamine-aziridine copolymer of average molecular weight of 800, and
- b) about 3 wt % of Poly(hexafluoropropylene oxide) monocarboxylic acid, chloro terminated [Cl—$(C_3F_6O)_n$—$CF_2$—COOH], and
- c) about 38 wt % perfluoropolyether; and
- d) about 33 wt % poly(tetrafluoroethylene);

formulation 37
- a) about 21 wt % of ethylenediamine-aziridine copolymer of average molecular weight of 800, and
- b) about 5 wt % 1, 3-pentanediamine, and
- c) about 3 wt % of Cl—$(C_3F_6O)_n$—$CF_2$—$CONH(CH_2)_m$—$(OCH_2CH_2)_n$—$(CH_2)_m$—H, and
- d) about 38 wt % perfluoropolyether; and
- e) about 33 wt % poly(tetrafluoroethylene);

formulation 38
- a) about 17 wt % of a 15:80:5 wt % mixture of formamide polyaziridine, water, and sodium formate, and
- b) about 2 wt % of Cl—$(C_3F_6O)_n$—$CF_2$—$CONH(CH_2)_m$—$(OCH_2CH_2)_n$—$(CH_2)_m$—H, and
- c) about 4 wt % water and
- d) about 31 wt % perfluoropolyether; and
- e) about 46 wt % poly(tetrafluoroethylene);

formulation 39
- a) about 23 wt % of a 15:80:5 wt % mixture of formamide polyaziridine, water, and sodium formate, and
- b) about 3 wt % of Cl—$(C_3F_6O)_n$—$CF_2$—$CONH(CH_2)_m$—$(OCH_2CH_2)_n$—$(CH_2)_m$—H, and
- c) about 35 wt % perfluoropolyether; and
- d) about 40 wt % poly(tetrafluoroethylene);

formulation 40
- a) about 20 wt % of a 15:80:5 wt % mixture of formamide polyaziridine, water, and sodium formate, and
- b) about 1 wt % of Poly(hexafluoropropylene oxide) monocarboxylic acid, chloro terminated [Cl—$(C_3F_6O)_n$—$CF_2$—COOH], and
- c) about 5 wt % water and
- d) about 38 wt % perfluoropolyether; and
- e) about 35 wt % poly(tetrafluoroethylene);

formulation 41
- a) about 25 wt % of a 15:80:5 wt % mixture of formamide polyaziridine, water, and sodium formate, and
- b) about 2 wt % of Poly(hexafluoropropylene oxide) monocarboxylic acid, chloro terminated [Cl—$(C_3F_6O)_n$—$CF_2$—COOH], and
- c) about 38 wt % perfluoropolyether; and
- d) about 35 wt % poly(tetrafluoroethylene);

formulation 42
- a) about 13 wt % of ethylenediamine-aziridine copolymer of average molecular weight of 800, and
- b) about 13 wt % of polyaziridine of average molecular weight of 25,000, and
- c) about 1.5 wt % of Poly(hexafluoropropylene oxide) monocarboxylic acid, chloro terminated [Cl—$(C_3F_6O)_n$—$CF_2$—COOH], and
- d) about 1.5 wt % of Cl—$(C_3F_6O)_n$—$CF_2$—$CONH(CH_2)_m$—$(OCH_2CH_2)_n$—$(CH_2)_m$—H, and
- e) about 38 wt % perfluoropolyether; and
- f) about 33 wt % poly(tetrafluoroethylene);

formulation 43
- a) about 5 wt % 1,3-pentanediamine, and
- b) about 1 wt % of Cl—$(C_3F_6O)_n$—$CF_2$—$CONH(CH_2)_m$—$(OCH_2CH_2)_n$—$(CH_2)_m$—H, and
- c) about 49 wt % perfluoropolyether; and
- d) about 45 wt % poly(tetrafluoroethylene);

formulation 44:
- a) about 5 wt % 1,3-pentanediamine, and
- b) about 1 wt % of Poly(hexafluoropropylene oxide) monocarboxylic acid, chloro terminated [Cl—$(C_3F_6O)_n$—$CF_2$—COOH], and
- c) about 49 wt % perfluoropolyether; and
- d) about 45 wt % poly(tetrafluoroethylene);

formulation 45
- a) about 13 wt % of polyaziridine of average molecular weight of 25,000, and
- b) about 13 wt % of ethylenediamine-aziridine copolymer of average molecular weight of 800, and
- c) about 3 wt % of Cl—$(C_3F_6O)_n$—$CF_2$—$CONH(CH_2)_m$—$(OCH_2CH_2)_n$—$(CH_2)_m$—H and
- d) about 38 wt % perfluoropolyether; and
- e) about 33 wt % poly(tetrafluoroethylene);

formulation 46
- a) about 13 wt % of polyaziridine of average molecular weight of 25,000, and
- b) about 13 wt % polyaziridine of average molecular weight of 1300, and
- c) about 3 wt % of Cl—$(C_3F_6O)_n$—$CF_2$—$CONH(CH_2)_m$—$(OCH_2CH_2)_n$—$(CH_2)_m$—H, and
- d) about 38 wt % perfluoropolyether; and
- e) about 33 wt % poly(tetrafluoroethylene);

formulation 47
- a) about 13 wt % of polyaziridine of average molecular weight of 25,000, and
- b) about 13 wt % hydroxyethylated polyaziridine with average molecular weight of 110,000, and
- c) about 3 wt % of Cl—$(C_3F_6O)_n$—$CF_2$—$CONH(CH_2)_m$—$(OCH_2CH_2)_n$—$(CH_2)_m$—H, and
- d) about 38 wt % perfluoropolyether; and
- e) about 33 wt % poly(tetrafluoroethylene);

formulation 48
- a) about 13 wt % of a 50:50 mixture of water and aziridine homopolymer of average molecular weight of 750,000, and
- b) about 13 wt % of polyaziridine of average molecular weight of 25,000, and
- c) about 3 wt % of Cl—$(C_3F_6O)_n$—$CF_2$—$CONH(CH_2)_m$—$(OCH_2CH_2)_n$—$(CH_2)_m$—H, and
- d) about 38 wt % perfluoropolyether; and
- e) about 33 wt % poly(tetrafluoroethylene);

formulation 49
- a) about 13 wt % of a 50:50 mixture of water and aziridine homopolymer of average molecular weight of 750,000, and
- b) about 13 wt % of ethylenediamine-aziridine copolymer of average molecular weight of 800, and
- c) about 3 wt % of Cl—$(C_3F_6O)_n$—$CF_2$—$CONH(CH_2)_m$—$(OCH_2CH_2)_n$—$(CH_2)_m$—H, and
- d) about 38 wt % perfluoropolyether; and
- e) about 33 wt % poly(tetrafluoroethylene);

formulation 50
- a) about 14 wt % of a 50:50 mixture of water and aziridine homopolymer of average molecular weight of 750,000, and
- b) about 13 wt % polyaziridine of average molecular weight of 1300, and
- c) about 3 wt % of Cl—$(C_3F_6O)_n$—$CF_2$—$CONH(CH_2)_m$—$(OCH_2CH_2)_n$—$(CH_2)_m$—H, and
- d) about 38 wt % perfluoropolyether; and
- e) about 33 wt % poly(tetrafluoroethylene);

formulation 51
- a) about 13 wt % of a 50:50 mixture of water and aziridine homopolymer of average molecular weight of 750,000, and
- b) about 13 wt % hydroxyethylated polyaziridine with average molecular weight of 110,000, and
- c) about 3 wt % of Cl—$(C_3F_6O)_n$—$CF_2$—$CONH(CH_2)_m$—$(OCH_2CH_2)_n$—$(CH_2)_m$—H, and
- d) about 38 wt % perfluoropolyether; and
- e) about 33 wt % poly(tetrafluoroethylene);

formulation 52
- a) about 13 wt % of ethylenediamine-aziridine copolymer of average molecular weight of 800, and
- b) about 13 wt % hydroxyethylated polyaziridine with average molecular weight of 110,000, and
- c) about 3 wt % of Cl—$(C_3F_6O)_n$—$CF_2$—$CONH(CH_2)_m$—$(OCH_2CH_2)_n$—$(CH_2)_m$—H, and
- d) about 38 wt % perfluoropolyether; and
- e) about 33 wt % poly(tetrafluoroethylene);

formulation 53
- a) about 13 wt % hydroxyethylated polyaziridine with average molecular weight of 110,000, and
- b) about 13 wt % polyaziridine of average molecular weight of 1300, and
- c) about 3 wt % of Cl—$(C_3F_6O)_n$—$CF_2$—$CONH(CH_2)_m$—$(OCH_2CH_2)_n$—$(CH_2)_m$—H, and
- d) about 38 wt % perfluoropolyether; and
- e) about 33 wt % poly(tetrafluoroethylene);

formulation 54
- a) about 11 wt % polyaziridine of average molecular weight of 1300, and
- b) about 12 wt % of ethylenediamine-aziridine copolymer of average molecular weight of 800, and
- c) about 3 wt % of Cl—$(C_3F_6O)_n$—$CF_2$—$CONH(CH_2)_m$—$(OCH_2CH_2)_n$—$(CH_2)_m$—H, and
- d) about 34 wt % perfluoropolyether; and
- e) about 40 wt % poly(tetrafluoroethylene);

formulation 55
- a) about 13 wt % of a 15:80:5 wt % mixture of formamide polyaziridine, water, and sodium formate, and
- b) about 13 wt % polyaziridine of average molecular weight of 1300, and
- c) about 3 wt % of Cl—$(C_3F_6O)_n$—$CF_2$—$CONH(CH_2)_m$—$(OCH_2CH_2)_n$—$(CH_2)_m$—H, and
- d) about 38 wt % perfluoropolyether; and
- e) about 33 wt % poly(tetrafluoroethylene);

formulation 56
- a) about 13 wt % of a 15:80:5 wt % mixture of formamide polyaziridine, water, and sodium formate, and
- b) about 13 wt % of polyaziridine of average molecular weight of 25,000, and
- c) about 3 wt % of Cl—$(C_3F_6O)_n$—$CF_2$—$CONH(CH_2)_m$—$(OCH_2CH_2)_n$—$(CH_2)_m$—H, and
- d) about 38 wt % perfluoropolyether; and
- e) about 33 wt % poly(tetrafluoroethylene);

formulation 57
- a) about 11 wt % of a 15:80:5 wt % mixture of formamide polyaziridine, water, and sodium formate, and
- b) about 12 wt % hydroxyethylated polyaziridine with average molecular weight of 110,000, and
- c) about 3 wt % of Cl—$(C_3F_6O)_n$—$CF_2$—$CONH(CH_2)_m$—$(OCH_2CH_2)_n$—$(CH_2)_m$—H, and
- d) about 34 wt % perfluoropolyether; and
- e) about 41 wt % poly(tetrafluoroethylene);

formulation 58
- a) about 12 wt % of a 15:80:5 wt % mixture of formamide polyaziridine, water, and sodium formate, and
- b) about 12 wt % of a 50:50 mixture of water and aziridine homopolymer of average molecular weight of 750,000, and
- c) about 3 wt % of Cl—$(C_3F_6O)_n$—$CF_2$—$CONH(CH_2)_m$—$(OCH_2CH_2)_n$—$(CH_2)_m$—H, and
- d) about 35 wt % perfluoropolyether; and
- e) about 38 wt % poly(tetrafluoroethylene);

formulation 59
- a) about 12 wt % of a 15:80:5 wt % mixture of formamide polyaziridine, water, and sodium formate, and
- b) about 12 wt % of ethylenediamine-aziridine copolymer of average molecular weight of 800, and
- c) about 3 wt % of Cl—$(C_3F_6O)_n$—$CF_2$—$CONH(CH_2)_m$—$(OCH_2CH_2)_n$—$(CH_2)_m$—H, and
- d) about 36 wt % perfluoropolyether; and
- e) about 37 wt % poly(tetrafluoroethylene);

formulation 60
- a) about 23 wt % of a 50.4 weight % aqueous solution of homopolymer of 2-propene-1-amine hydrochloride, and
- b) about 3 wt % of Poly(hexafluoropropylene oxide) monocarboxylic acid, chloro terminated [Cl—$(C_3F_6O)_n$—$CF_2$—COOH], and
- c) about 34 wt % perfluoropolyether; and
- d) about 41 wt % poly(tetrafluoroethylene);

formulation 61
  a) about 26 wt % of a 50.4 weight % aqueous solution of homopolymer of 2-propene-1-amine hydrochloride, and
  b) about 3 wt % of Cl—$(C_3F_6O)_n$—$CF_2$—$CONH(CH_2)_m$—$(OCH_2CH_2)_n$—$(CH_2)_m$—H, and
  c) about 38 wt % perfluoropolyether; and
  d) about 33 wt % poly(tetrafluoroethylene);
formulation 62
  a) about 19 wt % of a 10.3 weight % aqueous solution of homopolymer of 2-propene-1-amine, and
  b) about 1 wt % of Poly(hexafluoropropylene oxide) monocarboxylic acid, chloro terminated [Cl—$(C_3F_6O)_n$—$CF_2$—COOH], and
  c) about 28 wt % perfluoropolyether; and
  d) about 52 wt % poly(tetrafluoroethylene);
formulation 63
  a) about 18 wt % of a 10.3 weight % aqueous solution of homopolymer of 2-propene-1-amine, and
  b) about 2 wt % of Cl—$(C_3F_6O)_n$—$CF_2$—$CONH(CH_2)_m$—$(OCH_2CH_2)_n$—$(CH_2)_m$—H, and
  c) about 25 wt % perfluoropolyether; and
  d) about 55 wt % poly(tetrafluoroethylene);
formulation 64
  a) about 12 wt % of a 10.3 weight % aqueous solution of homopolymer of 2-propene-1-amine, and
  b) about 12 wt % of a 50.4 weight % aqueous solution of homopolymer of 2-propene-1-amine hydrochloride, and
  c) about 3 wt % Fluorolink 7005, and
  d) about 34 wt % perfluoropolyether; and
  e) about 40 wt % poly(tetrafluoroethylene);
formulation 65
  a) about 2 wt % DEAM (diethanolamine), and
  b) about 1 wt % Surfactant, and
  c) about 1 wt % water, and
  d) about 49 wt % perfluoropolyether; and
  e) about 46 wt % poly(tetrafluoroethylene);
formulation 66
  a) about 2 wt % DEAM, and
  b) about 1 wt % Surfactant, and
  c) about 1 wt % water, and
  d) about 48 wt % perfluoropolyether; and
  e) about 48 wt % poly(tetrafluoroethylene);
formulation 67
  a) about 2 wt % DEAM, and
  b) about 1 wt % Surfactant, and
  c) about 1 wt % water, and
  d) about 49 wt % perfluoropolyether; and
  e) about 47 wt % poly(tetrafluoroethylene);
formulation 68
  a) about 13 wt % of a 50:50 mixture of water and aziridine homopolymer of average molecular weight of 750,000, and
  b) about 13 wt % polyaziridine of average molecular weight of 1300, and
  c) about 1.5 wt % of Poly(hexafluoropropylene oxide) monocarboxylic acid, chloro terminated [Cl—$(C_3F_6O)_n$—$CF_2$—COOH], and
  d) about 1.5 wt % of Cl—$(C_3F_6O)_n$—$CF_2$—$CONH(CH_2)_m$—$(OCH_2CH_2)_n$—$(CH_2)_m$—H, and
  e) about 38 wt % perfluoropolyether; and
  f) about 33 wt % poly(tetrafluoroethylene);
formulation 69
  a) about 13 wt % of a 50:50 mixture of water and aziridine homopolymer of average molecular weight of 750,000, and
  b) about 13 wt % of ethylenediamine-aziridine copolymer of average molecular weight of 800, and
  c) about 1.5 wt % of Poly(hexafluoropropylene oxide) monocarboxylic acid, chloro terminated [Cl—$(C_3F_6O)_n$—$CF_2$—COOH], and
  d) about 1.5 wt % of Cl—$(C_3F_6O)_n$—$CF_2$—$CONH(CH_2)_m$—$(OCH_2CH_2)_n$—$(CH_2)_m$—H, and
  e) about 38 wt % perfluoropolyether; and
  f) about 33 wt % poly(tetrafluoroethylene);
formulation 70
  a) about 13 wt % polyaziridine of average molecular weight of 1300, and
  b) about 2 wt % of Cl—$(C_3F_6O)_n$—$CF_2$—$CONH(CH_2)_m$—$(OCH_2CH_2)_n$—$(CH_2)_m$—H, and
  c) about 44 wt % perfluoropolyether; and
  d) about 42 wt % poly(tetrafluoroethylene);
formulation 71
  a) about 6 wt % polyaziridine of average molecular weight of 1300, and
  b) about 1 wt % of Cl—$(C_3F_6O)_n$—$CF_2$—$CONH(CH_2)_m$—$(OCH_2CH_2)_n$—$(CH_2)_m$—H, and
  c) about 47 wt % perfluoropolyether; and
  d) about 46 wt % poly(tetrafluoroethylene);
formulation 72
  a) about 13 wt % of polyaziridine of average molecular weight of 25,000, and
  b) about 2 wt % of Cl—$(C_3F_6O)_n$—$CF_2$—$CONH(CH_2)_m$—$(OCH_2CH_2)_n$—$(CH_2)_m$—H, and
  c) about 44 wt % perfluoropolyether; and
  d) about 42 wt % poly(tetrafluoroethylene);
formulation 73
  a) about 6 wt % of polyaziridine of average molecular weight of 25,000, and
  b) about 1 wt % of Cl—$(C_3F_6O)_n$—$CF_2$—$CONH(CH_2)_m$—$(OCH_2CH_2)_n$—$(CH_2)_m$—H, and
  c) about 47 wt % perfluoropolyether; and
  d) about 46 wt % poly(tetrafluoroethylene);
formulation 74
  a) about 14 wt % polyaziridine of average molecular weight of 1300, and
  b) about 2 wt % of Poly(hexafluoropropylene oxide) monocarboxylic acid, chloro terminated [Cl—$(C_3F_6O)_n$—$CF_2$—COOH], and
  c) about 43 wt % perfluoropolyether; and
  d) about 41 wt % poly(tetrafluoroethylene);
formulation 75
  a) about 7 wt % polyaziridine of average molecular weight of 1300, and
  b) about 1 wt % of Poly(hexafluoropropylene oxide) monocarboxylic acid, chloro terminated [Cl—$(C_3F_6O)_n$—$CF_2$—COOH], and
  c) about 47 wt % perfluoropolyether; and
  d) about 45 wt % poly(tetrafluoroethylene);
formulation 76
  a) about 13 wt % of ethylenediamine-aziridine copolymer of average molecular weight of 800, and
  b) about 2 wt % of Poly(hexafluoropropylene oxide) monocarboxylic acid, chloro terminated [Cl—$(C_3F_6O)_n$—$CF_2$—COOH], and
  c) about 44 wt % perfluoropolyether; and
  d) about 42 wt % poly(tetrafluoroethylene);

formulation 77
  a) about 7 wt % of ethylenediamine-aziridine copolymer of average molecular weight of 800, and
  b) about 2 wt % of Poly(hexafluoropropylene oxide) monocarboxylic acid, chloro terminated [Cl—$(C_3F_6O)_n$—$CF_2$—COOH], and
  c) about 47 wt % perfluoropolyether; and
  d) about 46 wt % poly(tetrafluoroethylene);
formulation 78
  a) about 13 wt % of ethylenediamine-aziridine copolymer of average molecular weight of 800, and
  b) about 2 wt % of Cl—$(C_3F_6O)_n$—$CF_2$—$CONH(CH_2)_m$—$(OCH_2CH_2)_n$—$(CH_2)_m$—H with molecular weight range 1500-1700, and
  c) about 44 wt % perfluoropolyether; and
  d) about 41 wt % poly(tetrafluoroethylene);
formulation 79
  a) about 7 wt % of ethylenediamine-aziridine copolymer of average molecular weight of 800, and
  b) about 1 wt % of Cl—$(C_3F_6O)_n$—$CF_2$—$CONH(CH_2)_m$—$(OCH_2CH_2)_n$—$(CH_2)_m$—H, and
  c) about 47 wt % perfluoropolyether; and
  d) about 46 wt % poly(tetrafluoroethylene);
formulation 80
  a) about 7 wt % of ethylenediamine-aziridine copolymer of average molecular weight of 800, and
  b) about 7 wt % of polyaziridine of average molecular weight of 25,000, and
  c) about 1 wt % of Poly(hexafluoropropylene oxide) monocarboxylic acid, chloro terminated [Cl—$(C_3F_6O)_n$—$CF_2$—COOH], and
  d) about 1 wt % of Cl—$(C_3F_6O)_n$—$CF_2$—$CONH(CH_2)_m$—$(OCH_2CH_2)_n$—$(CH_2)_m$—H, and
  e) about 44 wt % perfluoropolyether; and
  f) about 42 wt % poly(tetrafluoroethylene);
formulation 81
  a) about 3 wt % of ethylenediamine-aziridine copolymer of average molecular weight of 800, and
  b) about 3 wt % of polyaziridine of average molecular weight of 25,000, and
  c) about 0.5 wt % of Poly(hexafluoropropylene oxide) monocarboxylic acid, chloro terminated [Cl—$(C_3F_6O)_n$—$CF_2$—COOH], and
  d) about 0.5 wt % of Cl—$(C_3F_6O)_n$—$CF_2$—$CONH(CH_2)_m$—$(OCH_2CH_2)_n$—$(CH_2)_m$—H, and
  e) about 49 wt % perfluoropolyether; and
  f) about 47 wt % poly(tetrafluoroethylene);
formulation 82
  a) about 13 wt % of a 50:50 mixture of water and aziridine homopolymer of average molecular weight of 750,000, and
  b) about 1.5 wt % of Cl—$(C_3F_6O)_n$—$CF_2$—$CONH(CH_2)_m$—$(OCH_2CH_2)_n$—$(CH_2)_m$—H, and
  c) about 45 wt % perfluoropolyether; and
  d) about 41 wt % poly(tetrafluoroethylene);
formulation 83
  a) about 6 wt % of a 50:50 mixture of water and aziridine homopolymer of average molecular weight of 750,000, and
  b) about 1 wt % of Cl—$(C_3F_6O)_n$—$CF_2$—$CONH(CH_2)_m(OCH_2CH_2)_n$—$(CH_2)_m$—H, and
  c) about 48 wt % perfluoropolyether; and
  d) about 45 wt % poly(tetrafluoroethylene)
formulation 84
  a) about 15 wt % of polyaziridine of average molecular weight of 25,000, and
  b) about 2 wt % of Poly(hexafluoropropylene oxide) monocarboxylic acid, chloro terminated [Cl—$(C_3F_6O)_n$—$CF_2$—COOH], and
  c) about 51 wt % perfluoropolyether; and
  d) about 33 wt % poly(tetrafluoroethylene);
formulation 85
  a) about 14 wt % of a 50:50 mixture of water and aziridine homopolymer of average molecular weight of 750,000, and
  b) about 2 wt % of Poly(hexafluoropropylene oxide) monocarboxylic acid, chloro terminated [Cl—$(C_3F_6O)_n$—$CF_2$—COOH], and
  c) about 48 wt % perfluoropolyether; and
  d) about 36 wt % poly(tetrafluoroethylene);
formulation 86
  a) about 17 wt % of polyaziridine of average molecular weight of 25,000, and
  b) about 1 wt % of Poly(hexafluoropropylene oxide) monocarboxylic acid, chloro terminated [Cl—$(C_3F_6O)_n$—$CF_2$—COOH], and
  c) about 50 wt % perfluoropolyether; and
  d) about 41 wt % poly(tetrafluoroethylene);
formulation 87
  a) about 7 wt % of a 50:50 mixture of water and aziridine homopolymer of average molecular weight of 750,000, and
  b) about 1 wt % of Poly(hexafluoropropylene oxide) monocarboxylic acid, chloro terminated [Cl—$(C_3F_6O)_n$—$CF_2$—COOH], and
  c) about 49 wt % perfluoropolyether; and
  d) about 43 wt % poly(tetrafluoroethylene);
formulation 88
  a) about 13 wt % of a 50:50 mixture of water and aziridine homopolymer of average molecular weight of 750,000, and
  b) about 13 wt % of polyaziridine of average molecular weight of 25,000, and
  c) about 1.5 wt % of Poly(hexafluoropropylene oxide) monocarboxylic acid, chloro terminated [Cl—$(C_3F_6O)_n$—$CF_2$—COOH with molecular weight of 600-700)], and
  d) about 1.5 wt % of Cl—$(C_3F_6O)_n$—$CF_2$—$CONH(CH_2)_m$—$(OCH_2CH_2)_n$—$(CH_2)_m$—H, and
  e) about 38 wt % perfluoropolyether; and
  about 33 wt % poly(tetrafluoroethylene);
formulation 89
  a) about 13 wt % polyaziridine of average molecular weight of 1300, and
  b) about 13 wt % of ethylenediamine-aziridine copolymer of average molecular weight of 800, and
  c) about 1.5 wt % of Poly(hexafluoropropylene oxide) monocarboxylic acid, chloro terminated [Cl—$(C_3F_6O)_n$—$CF_2$—COOH], and
  d) about 1.5 wt % of Cl$(C_3F_6O)_n$—$CF_2$—$CONH(CH_2)_m$—$(OCH_2CH_2)_n$—$(CH_2)_m$—H, and
  e) about 38 wt % perfluoropolyether; and
  f) about 33 wt % poly(tetrafluoroethylene);

formulation 90
  a) about 13 wt % polyaziridine of average molecular weight of 1300, and
  b) about 13 wt % of polyaziridine of average molecular weight of 25,000, and
  c) about 1.5 wt % of Poly(hexafluoropropylene oxide) monocarboxylic acid, chloro terminated [Cl—$(C_3F_6O)_n$—$CF_2$—COOH], and
  d) about 1.5 wt % of Cl—$(C_3F_6O)_n$—$CF_2$—CONH$(CH_2)_m$—$(OCH_2CH_2)_n$—$(CH_2)_m$—H, and
  e) about 38 wt % perfluoropolyether; and
  d) about 33 wt % poly(tetrafluoroethylene);
formulation 91
  a) about 10 wt % of a 50:50 mixture of water and aziridine homopolymer of average molecular weight of 750,000, and
  b) about 2 wt % of Poly(hexafluoropropylene oxide) monocarboxylic acid, chloro terminated [Cl—$(C_3F_6O)_n$—$CF_2$—COOH], and
  c) about 7 wt % water, and
  d) about 38 wt % perfluoropolyether; and
  e) about 43 wt % poly(tetrafluoroethylene); and
formulation 92
  a) about 15 wt % of a 50:50 mixture of water and aziridine homopolymer of average molecular weight of 750,000, and
  b) about 3 wt % of Poly(hexafluoropropylene oxide) monocarboxylic acid, chloro terminated [Cl—$(C_3F_6O)_n$—$CF_2$——COOH], and
  c) about 6 wt % water, and
  d) about 27 wt % perfluoropolyether; and
  e) about 49 wt % poly(tetrafluoroethylene).

2. The topical skin protectant formulation of claim 1, further comprising one or more additives.

3. The topical skin protectant formulation of claim 2, wherein said additives comprise one or more of water, surfactants, including:
  a. propene, 1,1,2,3,3,3-hexafluoro-, telomers with chlorotrifluoroethene, oxidized, reduced ,ethyl ester, hydrolyzed,
  b. perfluoropolyether derivative is PFPE-CONH—$(CH_2)_3$—$(OCH_2CH_3)_{18}$—$CH_3$,
  c. perfluoropolyether surfactant,
  d. stabilizers,
  e. camouflage paints, and
  f. sunscreens.

4. The topical skin protectant formulation of claim 1, having a viscosity is 20 cSt to 500 cSt.

5. The topical skin protectant formulation of claim 1, having a surface area of 6 $m^2/g$.

6. The topical skin protectant formulation of claim 1, wherein said active moiety is in said base cream as a solid or aqueous suspension.

* * * * *